US012589249B2

(12) United States Patent
Cao et al.

(10) Patent No.: US 12,589,249 B2
(45) Date of Patent: Mar. 31, 2026

(54) MEDICAL DEVICE AND METHOD FOR CARDIAC PACING OF THE HIS-PURKINJE CONDUCTION SYSTEM

(71) Applicant: Medtronic, Inc., Minneapolis, MN (US)

(72) Inventors: Jian Cao, San Jose, CA (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 415 days.

(21) Appl. No.: 18/085,955

(22) Filed: Dec. 21, 2022

(65) Prior Publication Data

US 2023/0233864 A1 Jul. 27, 2023

Related U.S. Application Data

(60) Provisional application No. 63/303,238, filed on Jan. 26, 2022.

(51) Int. Cl.
| | | |
|---|---|---|
| *A61N 1/365* | (2006.01) | |
| *A61N 1/362* | (2006.01) | |
| *A61N 1/368* | (2006.01) | |

(52) U.S. Cl.
CPC ................................ *A61N 1/36585* (2013.01)

(58) Field of Classification Search
CPC .............. A61N 1/36585; A61N 1/3627; A61N 1/36564; A61N 1/36578; A61N 1/3682
See application file for complete search history.

(56) References Cited

U.S. PATENT DOCUMENTS

| | | | |
|---|---|---|---|
| 6,882,882 B2 | 4/2005 | Struble et al. | |
| 7,269,460 B2 | 9/2007 | Chinchoy | |
| 7,320,676 B2 | 1/2008 | Miesel | |
| 7,591,185 B1 | 9/2009 | Mothilal et al. | |
| 8,118,748 B2 | 2/2012 | Schugt et al. | |
| 8,565,880 B2 | 10/2013 | Dong et al. | |
| 8,626,289 B2 | 1/2014 | Ding et al. | |
| 8,761,880 B2 | 6/2014 | Maskara et al. | |
| 8,825,155 B2 | 9/2014 | Zhu et al. | |
| 8,831,705 B2 | 9/2014 | Dobak | |

(Continued)

FOREIGN PATENT DOCUMENTS

| | | | |
|---|---|---|---|
| EP | 2164562 B1 | 10/2014 | |
| WO | WO-2012125273 A2 * | 9/2012 | ........... A61N 1/3627 |

OTHER PUBLICATIONS (PCT/IB2023/050060) PCT Notification of Transmittal of the International Search Report and the Written Opinion of the International Searching Authority, dated Mar. 3, 2023, 12 pages.

*Primary Examiner* — Brian T Gedeon

(57) ABSTRACT

A medical device is configured to deliver His-Purkinje pacing pulses according to multiple settings of a pacing control parameter and determine an electromechanical time delay from a ventricular electrical event to a fiducial point of the pressure signal for each of the pacing control parameter settings. The medical device may be configured to select an operating pacing control parameter from the pacing control parameter settings based on a determined electromechanical time delay being less than a threshold interval. The medical device may deliver pacing pulses to the His-Purkinje conduction system according to the selected operating pacing control parameter.

19 Claims, 10 Drawing Sheets

(56) References Cited

U.S. PATENT DOCUMENTS

| | | | |
|---|---|---|---|
| 8,954,147 B2 | 2/2015 | Arcot-Krishnamurthy et al. | |
| 10,065,042 B2 | 9/2018 | Ortega et al. | |
| 10,729,902 B1 | 8/2020 | Makharinsky et al. | |
| 11,007,369 B2 | 5/2021 | Sheldon et al. | |
| 11,964,160 B2 | 4/2024 | Zhou et al. | |
| 2012/0303078 A1* | 11/2012 | Li | A61B 7/00 |
| | | | 607/4 |
| 2015/0142071 A1* | 5/2015 | Min | A61N 1/36585 |
| | | | 607/18 |
| 2018/0021567 A1 | 1/2018 | An et al. | |
| 2019/0083800 A1 | 3/2019 | Yang et al. | |
| 2019/0111270 A1 | 4/2019 | Zhou | |
| 2020/0316386 A1 | 10/2020 | Demmer et al. | |
| 2022/0080210 A1 | 3/2022 | Cao et al. | |

* cited by examiner

200

202  SENSE CARDIAC SIGNALS

204  SET PACING DELAY INTERVAL

206  DELIVER PACING PULSE(S)

208  DETERMINE SIGNAL FEATURES

210  ANOTHER SETTING?   YES

NO

212  SELECT OPERATING PACING DELAY

214  ANOTHER PACING DELAY?

216  DELIVER HIS-PURKINJE PACING USING OPERATING PACING DELAY

300

302   SENSE CARDIAC SIGNALS

304   SET AV DELAY

306   DELIVER PACING PULSE(S)

308   DETERMINE MAX DP/DT

310   DETERMINE MAX DP/DT TIME(S)

312   ANOTHER SETTING?   YES

NO

314   IDENTIFY MAX DP/DT TIMES < THRESHOLD

316   SELECT OPERATING AV DELAY

318   DELIVER HIS-PURKINJE PACING USING OPERATING AV DELAY

500

502   SELECT PACING DELAY INTERVAL

504   DETERMINE OPTIMIZED SIGNAL FEATURE(S) AND/ OR TEMPLATE(S)

505   ESTABLISH OPTIMIZED SIGNAL CRITERIA

506   DELIVER HIS-PURKINJE PACING PULSE(S)

508   OPTIMIZED SIGNAL CRITERIA MET?   YES

NO

509   VERIFY HIS-PURKINJE CAPTURE

510   ADJUST PACING DELAY INTERVAL

MEDICAL DEVICE AND METHOD FOR CARDIAC PACING OF THE HIS-PURKINJE CONDUCTION SYSTEM

TECHNICAL FIELD

This disclosure relates to a medical device and method for delivering cardiac pacing to the His-Purkinje conduction system.

BACKGROUND

During normal sinus rhythm (NSR), the heartbeat is regulated by electrical signals produced by the sino-atrial (SA) node located in the right atrial wall. Each intrinsic atrial depolarization signal produced by the SA node spreads across the atria, causing the depolarization and contraction of the atria, and arrives at the atrioventricular (AV) node. The AV node responds by propagating a ventricular depolarization signal through the Bundle of His (or "His bundle") of the ventricular septum and thereafter to the Purkinje branches and the Purkinje muscle fibers of the right and left ventricles. This native conduction system including the His bundle, right and left branches (sometimes referred to as the right and left bundle branches) and the Purkinje fibers may be referred to as the "His-Purkinje conduction system" or "His-Purkinje system."

Patients with a conduction system abnormality, e.g., poor AV node conduction, poor SA node function, or other conduction abnormalities, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block or other conduction abnormalities to provide ventricular rate support.

Dual chamber pacemakers are available which include a transvenous atrial lead carrying electrodes which are placed in the right atrium and a transvenous ventricular lead carrying electrodes that are advanced through the right atrium into the right ventricle. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Cardiac pacing of the His-Purkinje system has been proposed to provide ventricular pacing along the heart's native conduction system. Chronic ventricular pacing via electrodes at or near the right ventricular apex may be associated with increased risk of atrial fibrillation or heart failure. Alternative pacing sites have been investigated or proposed, such as pacing the at or near the His bundle. Pacing the ventricles via the His-Purkinje system of the heart allows recruitment along the heart's natural conduction system and is hypothesized to promote more physiologically normal cardiac activation than other pacing sites, such as the ventricular apex.

SUMMARY

The techniques of this disclosure generally relate to a medical device configured to deliver His-Purkinje pacing pulses. A medical device operating according to techniques disclosed herein may deliver His-Purkinje pacing pulses according to multiple pacing control parameter settings and determine an electromechanical time delay from a ventricular electrical event to a fiducial point of cardiac mechanical signal for each of the pacing control parameter settings. The medical device may be configured to select an operating pacing control parameter from the pacing control parameter settings based on at least the determined electromechanical time delays. The medical device may deliver pacing pulses to the His-Purkinje conduction system according to the selected operating pacing control parameter.

In some examples, the medical device is configured to receive a pressure signal for determining the electromechanical time delays between a ventricular electrical event and a fiducial point of the pressure signal, such as a time of a maximum positive slope of the pressure signal. The medical device may be configured to select a pacing delay interval, e.g., an AV delay or an interventricular delay, used to control the timing of His-Purkinje pacing pulses based on the electromechanical time delay. Other examples of cardiac mechanical signal features and pacing control parameters that may be selected based on cardiac mechanical signal features are described in conjunction with the accompanying drawings.

In one example, the disclosure provides a medical device including a therapy delivery circuit configured to deliver at least one His-Purkinje pacing pulse according to each one of multiple settings of a pacing control parameter. The medical device further includes a pressure sensor configured to sense a pressure signal and a processing circuit configured to, for each of the pacing control parameter settings, identify a ventricular electrical event, identify a fiducial point of the pressure signal following the ventricular electrical event and determine an electromechanical time delay from the ventricular electrical event to the fiducial point of the pressure signal. The processing circuit may be configured to identify each of the pacing control parameter settings that is associated with a determined electromechanical time delay that is less than a threshold interval. The processing circuit may be configured to select an operating pacing control parameter from the identified pacing control parameter settings. The therapy delivery circuit is configured to deliver His-Purkinje pacing according to the selected operating pacing control parameter In another example, the disclosure provides a method performed by a medical device including delivering at least one His-Purkinje pacing pulse according to each one of multiple pacing control parameter settings. The method further includes sensing a pressure signal from a pressure sensor and, for each of the multiple control parameter settings, identifying a ventricular electrical event, identifying a fiducial point of the pressure signal following the ventricular electrical event, and determining an electromechanical time delay from the ventricular electrical event to the fiducial point of the pressure signal. The method may further include identifying each of the pacing control parameter settings that is associated with a determined electromechanical time delay that is less than a threshold interval and selecting an operating pacing control parameter from the identified pacing control parameter settings. The method may further include delivering His-Purkinje pacing pulses according to the selected operating pacing control parameter.

In yet another example, the disclosure provides a non-transitory, computer-readable storage medium comprising a set of instructions which, when executed by a processing circuit of a medical device, cause the medical device to deliver at least one His-Purkinje pacing pulse according to each one of multiple pacing control parameter settings, sense a pressure signal by a pressure sensor, and for each of the pacing control parameter settings identify a ventricular electrical event, identify a fiducial point of the pressure signal following the ventricular electrical event; and determine an electromechanical time delay from the ventricular electrical event to the fiducial point of the pressure signal. The instructions may further cause the medical device to identify each of the pacing control parameter settings that is associated with a determined electromechanical time delay that is less than a threshold interval and select an operating pacing control parameter from the identified pacing control parameter settings. The instructions may further cause the medical device to deliver His-Purkinje pacing pulses according to the selected operating pacing control parameter.

Further disclosed herein is the subject matter of the following clauses:

1. A medical device, comprising:
a therapy delivery circuit configured to deliver at least one His-Purkinje pacing pulse according to each of a plurality of settings of a pacing control parameter;
a pressure sensor configured to sense a first pressure signal; and
a processing circuit configured to:
for each of the plurality of settings of the pacing control parameter:
identify a ventricular electrical event;
identify a fiducial point of the first pressure signal following the ventricular electrical event;
determine an electromechanical time delay from the ventricular electrical event to the fiducial point of the first pressure signal;
identify from among the plurality of settings of the pacing control parameter each pacing control parameter setting that is associated with a determined electromechanical time delay that is less than a threshold interval; and
select an operating pacing control parameter from the identified pacing control parameter settings;
wherein the therapy delivery circuit is configured to deliver His-Purkinje pacing pulses according to the selected operating pacing control parameter.

2. The medical device of clause 1, wherein the processing circuit is further configured to identify the fiducial point of the first pressure signal by determining a maximum slope of the first pressure signal.

3. The medical device of any of clauses 1-2, further comprising a sensing circuit configured to sense a cardiac electrical signal;
wherein the processing circuit is further configured to identify the ventricular electrical event as one of:
a pacing pulse delivered by the therapy delivery circuit; or
a reference point of a QRS waveform of the cardiac electrical signal.

4

4. The medical device of any of clauses 1-3, wherein the processing circuitry is further configured to select the operating pacing control parameter by:
for each of the identified pacing control parameter settings associated with a determined electromechanical time delay that is less than the threshold interval, determining a maximum slope amplitude of the pressure signal; and
select the operating pacing control parameter as one of the identified pacing control parameter settings that is associated with a greatest maximum slope amplitude of the determined maximum slope amplitudes.

5. The medical device of any of clauses 1-4, wherein:
the pressure sensor is further configured to sense a second pressure signal; and
the processing circuitry is further configured to:
for each of the plurality of settings of the pacing control parameter, determine a mechanical delay time from a first point of the first pressure signal to a second point of the second pressure signal;
determine a minimum mechanical delay time from the determined mechanical delay times; and
select the operating pacing control parameter as one of the identified pacing control parameter settings that is associated with the minimum mechanical delay time.

6. The medical device of any of clauses 1-5, wherein the processing circuitry is further configured to identify each of the pacing control parameter settings from among the plurality of settings of the pacing control parameter that is associated with a determined electromechanical time delay that is less than the threshold interval and greater than a minimum threshold interval.

7. The medical device of any of clauses 1-6, further comprising a second sensor for sensing a second signal;
wherein the processing circuit is further configured to:
determine a feature of the second signal sensed following a His-Purkinje pacing pulse delivered according to the operating pacing control parameter;
determine that optimized signal criteria are not met by the feature of the second signal; and
adjust the operating pacing control parameter in response to the optimized signal criteria not being met.

8. The medical device of clause 7, wherein the second sensor comprises one of a second pressure sensor configured to sense a second pressure signal or an accelerometer configured to sense an acceleration signal.

9. The medical device of any of clauses 7-8, wherein the processing circuit is further configured to, in response to selecting the operating pacing control parameter, establish the optimized signal criteria based on an analysis of the second signal sensed by the second sensor following at least one His-Purkinje pacing pulse delivered by the therapy delivery circuit according to the selected operating pacing control parameter.

10. The medical device of any of clauses 1-9, wherein:
the therapy delivery circuit is configured to deliver at least one His-Purkinje pacing pulse at each of the plurality of settings of the pacing control parameter by delivering at least one His-Purkinje pacing pulse at an expiration of each of a plurality of atrioventricular delay settings; and
the processing circuit is configured to select the operating pacing control parameter from the identified pacing control parameter settings by selecting an operating atrioventricular delay.

11. The medical device of clause 10, wherein:

the therapy delivery circuit is further configured to:

generate the His-Purkinje pacing pulses for delivery to a first pacing site;

generate second ventricular pacing pulses for delivery to a second pacing site different than the first pacing site; and deliver His-Purkinje pacing pulses according to each of a plurality of inter-ventricular delay settings relative to the second ventricular pacing pulses; and the processing circuit is further configured to:

for each of the plurality of inter-ventricular delay settings, determine a feature of the first pressure signal; and select an operating inter-ventricular delay based on the determined features of the first pressure signal; and the therapy delivery circuit is configured to:

deliver the His-Purkinje pacing pulses according to the operating pacing control parameter by delivering each His-Purkinje pacing pulse at an expiration of the selected operating atrioventricular delay; and deliver the second ventricular pacing pulses at the operating inter-ventricular delay relative to each of the His-Purkinje pacing pulses.

12. The medical device of any of clauses 1-9, wherein:

the therapy delivery circuit is further configured to:

generate the His-Purkinje pacing pulses for delivery to a first pacing site;

generate second ventricular pacing pulses for delivery to a second pacing site different than the first pacing site; and deliver at least one His-Purkinje pacing pulse according to each of the plurality of settings of the pacing control parameter by delivering at least one His-Purkinje pacing pulse at each of a plurality of inter-ventricular delay settings relative to the second ventricular pacing pulses; and the processing circuit is further configured to select the operating pacing control parameter from the identified pacing control parameter settings by selecting an operating inter-ventricular delay.

13. A method, comprising:

delivering at least one His-Purkinje pacing pulse according to each of a plurality of settings of a pacing control parameter;

sensing a first pressure signal;

for each of the plurality of settings of the pacing control parameter:

identifying a ventricular electrical event;

identifying a fiducial point of the first pressure signal following the ventricular electrical event; and determining an electromechanical time delay from the ventricular electrical event to the fiducial point of the first pressure signal;

identifying from among the plurality of settings of the pacing control parameter each of the pacing control parameter settings that is associated with a determined electromechanical time delay that is less than a threshold interval;

selecting an operating pacing control parameter from the identified pacing control parameter settings; and delivering His-Purkinje pacing pulses according to the selected operating pacing control parameter.

14. The method of clause 13, further comprising identifying the fiducial point of the first pressure signal by determining a maximum slope of the first pressure signal.

15. The method of any of clauses 13-14, further comprising:

sensing a cardiac electrical signal; and identifying the ventricular electrical event as one of:

a pacing pulse delivered by the therapy delivery circuit; or a fiducial point of a QRS waveform of the cardiac electrical signal.

16. The method of any of clauses 13-15, further comprising selecting the operating pacing control parameter by:

for each of the identified pacing control parameter settings associated with a determined electromechanical time delay that is less than the threshold interval, determining a maximum slope amplitude of the pressure signal; and select the operating pacing control parameter as one of the identified pacing control parameter settings that is associated with a greatest maximum slope amplitude of the determined maximum slope amplitudes.

17. The method of any of clauses 13-16, further comprising:

sensing a second pressure signal; and for each of the plurality of settings of the pacing control parameter, determining a mechanical delay time from a first point of the first pressure signal to a second point of the second pressure signal;

determining a minimum mechanical delay time from the determined mechanical delay times; and selecting the operating pacing control parameter as one of the identified pacing control parameter settings that is associated with the minimum mechanical delay time.

18. The method of any of clauses 13-17, further comprising identifying each of the pacing control parameter settings that is associated with a determined electromechanical time delay that is less than the threshold interval and greater than a minimum threshold interval.

19. The method of any of clauses 13-18, further comprising:

sensing a second signal;

determining a feature of the second signal sensed following a His-Purkinje pacing pulse delivered according to the operating pacing control parameter;

determining that optimized signal criteria are not met by the feature of the second signal; and adjusting the operating pacing control parameter in response to the optimized signal criteria not being met.

20. The method of clause 19, wherein sensing the second signal comprises sensing one of a second pressure signal or an acceleration signal.

21. The method of any of clauses 19-21, further comprising, in response to selecting the operating pacing control parameter, establishing the optimized signal criteria based on an analysis of the second signal following at least one His-Purkinje pacing pulse delivered according to the selected operating pacing control parameter.

22. The method of any of clauses 13-21, further comprising:

delivering at least one His-Purkinje pacing pulse at each of the plurality of settings of the pacing control parameter by delivering at least one His-Purkinje pacing pulse at an expiration of each of a plurality of atrioventricular delay settings; and selecting the operating pacing control parameter from the identified pacing control parameter settings by selecting an operating atrioventricular delay.

23. The method of clause 22, further comprising:
generating the His-Purkinje pacing pulses for delivery to a first pacing site;
generating second ventricular pacing pulses for delivery to a second pacing site different than the first pacing site;
delivering His-Purkinje pacing pulses according to each of a plurality of inter-ventricular delay settings relative to the second ventricular pacing pulses;
for each of the plurality of inter-ventricular delay settings, determining a feature of the first pressure signal; and
selecting an operating inter-ventricular delay based on the determined features of the first pressure signal; and
delivering the His-Purkinje pacing pulses according to the operating pacing control parameter by delivering each His-Purkinje pacing pulse at an expiration of the selected operating atrioventricular delay; and
delivering the second ventricular pacing pulses at the operating inter-ventricular delay relative to each of the His-Purkinje pacing pulses.

24. The method of any of clauses 13-21, further comprising:
generating the His-Purkinje pacing pulses for delivery to a first pacing site;
generating second ventricular pacing pulses for delivery to a second pacing site different than the first pacing site;
delivering at least one His-Purkinje pacing pulse according to each of the plurality of settings of the pacing control parameter by delivering at least one His-Purkinje pacing pulse at each of a plurality of inter-ventricular delay settings relative to the second ventricular pacing pulses; and
selecting the operating pacing control parameter from the identified pacing control parameter settings by selecting an operating inter-ventricular delay.

25. A non-transitory, computer-readable storage medium comprising a set of instructions which, when executed by a processing circuit of a medical device cause the medical device to:
deliver at least one His-Purkinje pacing pulse according to each of a plurality of settings of a pacing control parameter;
sense a pressure signal;
for each of the plurality of settings of the pacing control parameter:
identify a ventricular electrical event;
identify a fiducial point of the pressure signal following the ventricular electrical event; and
determine an electromechanical time delay from the ventricular electrical event to the fiducial point of the pressure signal;
identify from among the plurality of settings of the pacing control parameter each of the pacing control parameter settings that is associated with a determined electromechanical time delay that is less than a threshold interval;
select an operating pacing control parameter from the identified pacing control parameter settings; and
deliver His-Purkinje pacing pulses according to the selected operating pacing control parameter.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
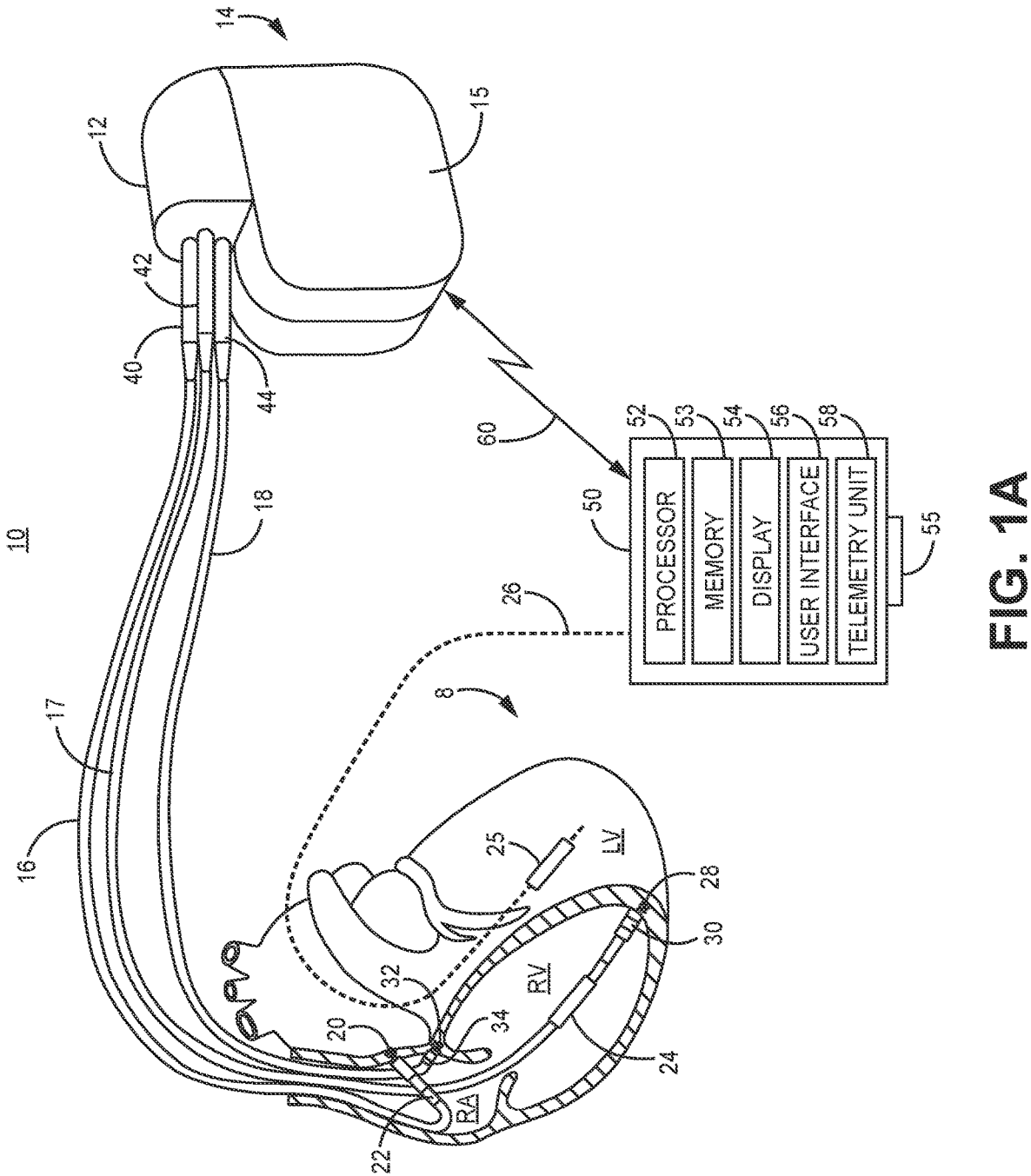
FIG. 1A is a conceptual diagram of a medical device system capable of sensing cardiac electrical signals and delivering His-Purkinje system pacing.

Examples of a medical device capable of generating pacing pulses for delivery to the His-Purkinje conduction system of a patient's heart are described herein. The medical device may be configured to receive a pressure signal for use in determining optimal His-Purkinje pacing parameter(s) according to the presently disclosed techniques. As used herein, the term "His-Purkinje," which may be used to refer to "His-Purkinje pacing," "His-Purkinje pacing pulses," "His-Purkinje capture," etc., may refer collectively to any portion of the His-Purkinje conduction system, which includes the His bundle, right and left-Purkinje branches and the Purkinje fibers, such that "His-Purkinje pacing" may refer generally to pacing anywhere along the His-Purkinje conduction system, and "His-Purkinje pacing pulses" refers to pacing pulses delivered anywhere along the His-Purkinje conduction system. "His-Purkinje capture" refers to capture of any portion of the His-Purkinje conduction system, which may be capture at or inferior to the His bundle, e.g., along a left and/or right bundle branch, and is also referred to herein as "His-Purkinje system capture."

A cardiac tissue is "captured" by a pacing pulse having sufficient electrical energy to cause depolarization of the cardiac tissue at the pacing site, causing an electrical "evoked response." The pacing-evoked depolarization at the pacing site is subsequently conducted through the heart's natural conduction system and/or myocardial tissue resulting in mechanical contraction of the heart chamber(s). In order to effectively capture and pace the heart to achieve a desired therapeutic effect, cardiac pacing pulses need to have a pulse energy that is equal to or greater than the capture threshold of the cardiac tissue at the pacing site. A pacing capture threshold test may be performed to determine the minimum pacing pulse amplitude for a given pacing pulse width (or vice versa) that captures the heart chamber. Determination of the capture threshold enables proper programming of the pacing pulse amplitude and pulse width to promote effective pacing and avoid loss of capture. Capture monitoring by the pacemaker at least periodically during ongoing pacing pulse delivery according to a pacing therapy allows automatic adjustments to the pacing pulse amplitude and/or pulse width to a suprathreshold value when loss of capture or a change in capture type is detected.

His-Purkinje system capture may include complete capture of the His bundle or partial capture of the His bundle. When pacing pulses are delivered by electrodes positioned in the heart to pace the His-Purkinje conduction system it may be possible to capture only the His-Purkinje system, capture both the His-Purkinje system and surrounding ventricular myocardium, or capture the surrounding ventricular myocardium without capturing the His-Purkinje system. Capture of only the His-Purkinje system can be referred to herein as "selective" His-Purkinje system (SHP) capture. Capture of the His-Purkinje system and surrounding ventricular myocardial tissue can be referred to as "non-selective" His-Purkinje system (NSHP) capture. Capture of the surrounding ventricular myocardium without capturing the His-Purkinje system can be referred to as ventricular myocardial (VM) capture. When the pacing pulse energy is below both the His-Purkinje system capture threshold and the VM capture threshold, a loss of capture occurs.

Once capture of a targeted portion of the His-Purkinje system is achieved, other His-Purkinje pacing control parameters can be optimized for promoting electrical and mechanical synchrony of the heart chambers. For example, a pacing delay used to control the timing of His-Purkinje pacing pulses adjusted to promote heart chamber synchrony and optimize the hemodynamic function of the heart. The AV delay is a time interval between an atrial event and the subsequent ventricular pacing pulse delivered to the His-Purkinje system for depolarizing the ventricles in synchrony with the atria. The atrial event may be an atrial pacing pulse delivered by the pacing device. In other instances, the atrial event may be an intrinsic atrial P-wave (or atrial mechanical contraction) sensed by the pacing device from a sensed cardiac signal.

In some examples, a medical device configured to deliver His-Purkinje pacing pulses may be configured to deliver pacing pulses to the patient's ventricles at a second pacing site. The medical device may set an inter-ventricular (VV) pacing delay for controlling the relative timing of pacing pulses delivered at a His-Purkinje pacing site and at a second ventricular pacing site, which may be a second His-Purkinje pacing site or a ventricular myocardial pacing site.

As disclosed herein, a pressure sensor configured for implantation in a ventricular chamber may be used to sense a ventricular pressure signal by a medical device configured to deliver His-Purkinje pacing pulses. The medical device operating according to techniques disclosed herein may analyze the pressure signal for determining optimal His-Purkinje pacing parameters, such as a pacing delay, which may include an AV delay and/or a VV delay.

FIG. 1A is a conceptual diagram of a medical device system 10 capable of pacing and sensing in a patient's heart 8. The system 10 includes implantable medical device (IMD) 14 coupled to a patient's heart 8 via transvenous electrical leads 16, 17 and 18. IMD 14 is shown as a dual chamber device capable of delivering cardiac pacing pulses and sensing cardiac electrical signals from the right atrium (RA) and from the ventricular chambers, e.g., the right ventricle (RV) and/or the left ventricle (LV), from an RA approach. Housing 15 encloses internal circuitry corresponding to the various circuits and components described in conjunction with FIG. 3 below, for sensing cardiac signals from heart 8 and controlling cardiac pacing therapy delivery using the techniques disclosed herein.

IMD 14 includes a connector block 12 that may be configured to receive the proximal ends of a RA lead 16 and a His-Purkinje lead 18, which are advanced transvenously for positioning electrodes for sensing and stimulation in the atria and ventricles. RA lead 16 is positioned such that its distal end is in the vicinity of the right atrium. RA lead 16 carries pacing and sensing electrodes 20 and 22, shown as a tip electrode 20 and a ring electrode 22 spaced proximally from tip electrode 20. The electrodes 20 and 22 provide sensing and pacing in the right atrium and are each connected to a respective insulated conductor extending within the elongated body of RA lead 16. Each insulated conductor is coupled at its proximal end to a connector carried by proximal lead connector 40. Connector block 12 is configured to receive lead connector 40 for electrically coupling conductors extending from the distal electrodes 20 and 22 to circuitry within housing 15 via electrical feedthroughs crossing housing 15.

His-Purkinje lead 18 may be advanced within the right atrium to position electrodes 32 and 34 for pacing and sensing in the vicinity of the His-Purkinje system, e.g., at or near the His bundle, from a right atrial approach, as shown. His-Purkinje lead tip electrode 32 may be a helical electrode that is advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the native His-Purkinje conduction system.

An intracardiac electrogram (EGM) signal may be produced by cardiac electrical signal sensing circuitry included in IMD 14 from the cardiac electrical signal received via tip electrode 32 and ring electrode 34 of His-Purkinje lead 18. The electrodes 32 and 34 are coupled to respective insulated conductors extending within the elongated body of His-Purkinje lead 18, which provide electrical connection to the proximal lead connector 44 coupled to internal IMD circuitry via connector block 12.

In addition to pacing and sensing capabilities, IMD 14 may be capable of delivering high voltage cardioversion or defibrillation (CV/DF) shocks in some examples. In this case, IMD 14 may be coupled to a lead carrying defibrillation electrodes, which may be elongated coil electrodes used to deliver high voltage CV/DF shocks. Defibrillation electrodes may be carried by RA lead 16, His-Purkinje lead 18 and/or another lead that may be coupled to IMD 14 via connector block 12. IMD housing 15 may function as an active electrode during CV/DF shock delivery in conjunction with defibrillation coil electrodes carried by one or more leads coupled to IMD 14.

Housing 15 may function as a return electrode for unipolar sensing or pacing configurations with any of the electrodes carried by leads 16 and 18. Electrodes 32 and 34 may be used in a bipolar pacing electrode pair for delivering His-Purkinje pacing pulses and for receiving a cardiac electrical signal for sensing intrinsic and pacing evoked QRS waveforms. In some examples, IMD 14 may be configured to sense a far field cardiac signal, e.g., using electrode 34 and housing 15 and a near field cardiac signal, e.g., using electrodes 32 and 34, for processing and analysis for detecting the type of capture following a delivered His-Purkinje pacing pulse as generally disclosed in U.S. patent application Ser. No. 17/533,005 (Cao, et al.), incorporated herein by reference in its entirety.

It is to be understood that although IMD 14 is described as a dual chamber pacemaker capable of sensing and pacing the RA and sensing ventricular signals and pacing the ventricular chambers via the His-Purkinje system, with or without CV/DF shock capabilities, IMD 14 may be a single chamber pacing device with single chamber or dual chamber sensing. For example, IMD 14 may be coupled only to His-Purkinje lead 18 for sensing atrial and/or ventricular electrical signals and delivering His-Purkinje pacing pulses for at least maintaining a minimum ventricular rate. His-Purkinje lead 18 may carry additional sensing electrodes positioned within the RA when lead 18 is positioned for delivering His-Purkinje pacing pulses such that IMD 14 is capable of dual chamber (atrial and ventricular) sensing and delivery of atrial synchronized ventricular pacing via the His-Purkinje system.

In some examples, IMD 14 may be further coupled to a pressure sensing lead 17, which may be advanced into the RV or the LV. In the example shown, pressure sensing lead 17 includes a pressure sensor 24 that is configured to be advanced within the RV for sensing an RV pressure signal. Lead 17 may optionally carry one or more pacing and/or sensing electrodes. For the sake of illustration, pressure sensing lead 17 is shown carrying a helical tip electrode 28, which may function as a pacing and sensing electrode and as a fixation member for anchoring pressure lead 17 in an RV location. A ring electrode 30 spaced proximally from tip electrode 28 may be used in combination with tip electrode 28 for delivering RV pacing pulses and sensing an RV cardiac electrical signal in some examples. However, RV pacing and sensing from the pressure lead 17 may be optional when implanted in combination with the His-Purkinje lead 18.

Furthermore, pressure lead 17 may carry one or more coil electrodes (not shown) for delivering high voltage shock pulses. As indicated above, or more of RA lead 16, pressure sensing lead 17, and/or His-Purkinje lead 18 may include one or more coil electrodes for delivering CV/DF shock pulses. IMD 14 may be implemented as an implantable cardioverter defibrillator (ICD) capable of detecting tachyarrhythmia, e.g., ventricular tachycardia and/or fibrillation, and delivering CV/DF shock pulses for terminating tachyarrhythmias in addition to delivering cardiac pacing therapies via the His-Purkinje system. As such, in any of the example IMD lead and electrode configurations shown and described herein, one or more leads coupled to IMD 14 may carry one or more coil electrodes that can be utilized for high voltage shock delivery.

Pressure sensor 24 may be a piezoelectric, piezoresistive, capacitive, inductive, electromagnetic, optical, micro-electromechanical system (MEMS), or another type of pressure sensor configured for implantation within blood. Various examples of pressure sensors that may be implemented in pressure lead 17 are generally disclosed in U.S. Pat. No. 8,118,748 (Schugt, et al.), U.S. Pat. No. 7,591,185 (Mothilal, et al.), U.S. Pat. No. 7,320,676 (Miesel), and U.S. Publication No. 2019/0111270 (Zhou), all of which are incorporated herein by reference in their entirety. The techniques disclosed herein are not limited to a particular type or form of pressure sensor and a variety of pressure sensors available for implementation in an implantable medical device may be incorporated in pressure lead 17 for acute and/or chronic pressure sensing.

In the example shown, pressure sensor 24 is coupled to conductors extending between pressure sensor 24 and proximal connector 42 within pressure lead 17 to provide electrical connection via connector block 12 to circuitry enclosed by housing 14 for carrying signals to pressure sensor 24 for enabling pressure sensor 24 to sense pressure in the RV and transmit a pressure signal back to circuitry within IMD 14. In other examples, pressure lead 17 may be advanced within the LV for sensing an LV pressure signal. In some examples, a first pressure lead may be advanced within the RV, and a second pressure lead may be advanced within the LV for sensing both an RV pressure signal and an LV pressure signal.

In some examples, medical device system 10 may include a temporary pressure lead 26 that may be advanced within the RV or the LV. In other examples, a temporary pressure lead may be advanced within each of the RV and the LV. In the illustrative example of FIG. 1A, temporary pressure lead 26 is advanced from an arterial approach, e.g., via the femoral artery, through the aorta and into the LV for positioning a pressure sensor 25 for sensing an LV pressure signal. In some examples, lead 17 carrying pressure sensor 24 and/or lead 26 carrying pressure sensor 25 may correspond to a commercially available pressure wire, e.g., the ZURICH PRESSURE GUIDEWIRE SYSTEM MODEL 100™ (available from Zurich Medical, U.S.A.), COMET™ II Pressure Guidewire (available from Boston Scientific, U.S.A.), or the VERRATA PLUS™ Pressure Guidewire (available from Philips, The Netherlands). The pressure lead 17 and/or 26 may be coupled to an external monitor. In the example shown, the temporary pressure lead 26 is shown coupled to an external device 50 which may be configured to receive the pressure signal for processing and analysis according to techniques disclosed herein. In other examples, the temporary pressure lead 26 may be coupled to an external pressure monitor which may transmit the pressure signal to external device 50, e.g., via a wired or wireless connection. The RV and/or LV pressure signals may be processed and analyzed for determining an optimal setting for one or more His-Purkinje pacing control parameters as further described below.

An external device 50 is shown in telemetric communication with IMD 14 by a communication link 60. External device 50 may be embodied as a programmer used in a hospital, clinic or physician's office to retrieve data from IMD 14 and to program operating parameters and algorithms in IMD 14 for controlling IMD functions. External device 50 may alternatively be embodied as a home monitor or handheld device for retrieving data from IMD 14. External device 50 may be used to program cardiac signal sensing parameters, cardiac rhythm detection parameters, cardiac pacing and CV/DF therapy control parameters and capture detection control parameters used by IMD 14.

External device 50 may include a processor 52, memory 53, display unit 54, user interface 56 and telemetry unit 58. Processor 52 controls external device operations and may processes data and signals received from IMD 14. Processor 52 may be configured to control telemetry unit 58 to transmit user-entered programming commands to IMD 14 and process data received from IMD 14 for display by display unit 54.

Display unit 54, which may include a graphical user interface, displays data and other information to a user for reviewing IMD operation and programmed parameters and may display programmable parameters to a user for selection and programming of IMD 14. Display unit 54 may generate a display of the cardiac electrical signals and/or pressure signals received from IMD and/or data derived therefrom. Display unit 54 may be configured to generate a graphical user interface (GUI) including various windows, icons, user selectable menus, etc. to facilitate interaction by a user with the external device 50. Display unit 54 may function as an input and/or output device using technologies including liquid crystal displays (LCD), quantum dot display, dot matrix displays, light emitting diode (LED) displays, organic light-emitting diode (OLED) displays, cathode ray tube displays, e-ink, or monochrome, color, or any other type of display capable of generating tactile, audio, and/or visual output. In some examples, display unit 54 is a presence-sensitive display that may serve as a user interface device that operates both as one or more input devices and one or more output devices.

User interface 56 may include a mouse, touch screen, keypad or the like to enable a user to interact with external device 50 to initiate a telemetry session with IMD 14 for retrieving data from and/or transmitting data to IMD 14. Programmable parameter setting may be transmitted to IMD 14 for controlling pacing capture determination, monitoring and analysis of ventricular pressure signals, His-Purkinje pacing pulse amplitude, pulse width, pacing lower rate, AV delay, VV delay or other programmable control parameters. Telemetry unit 58 includes a transceiver and antenna configured for bidirectional communication with a telemetry circuit included in IMD 14 and is configured to operate in conjunction with processor 52 for sending and receiving data relating to IMD functions via communication link 60, which may include data relating to His-Purkinje system pacing and optimization of pacing control parameters.

Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes, delivered therapies, and capture threshold determinations and/or optimized His-Purkinje pacing parameters and/or associated data may be retrieved from IMD 14 by external device 50 following an interrogation command.

External device 50 may include external ports 55 for electrical connection to surface ECG leads and electrodes (not shown in FIG. 1A) that may be coupled to a patient implanted with IMD 14. Processor 52 may receive ECG signals for display by display unit 54 for observation by a user during His-Purkinje system pacing. Observation of ECG signals may enable a user to confirm capture of the His-Purkinje system based on improvements in the QRS signals following delivered pacing pulses, such as narrowed QRS signals and/or decreased activation times between evoked QRS waveforms in the RV and in the LV indicating a more synchronous depolarization of the left and right ventricles or the disappearance of QRS abnormalities such as QRS features indicative of left bundle branch block, right bundle branch block or other ventricular conduction abnormalities. Observation of QRS signals by a user and/or analysis of QRS signal features by processor 52, which may be performed in combination with analysis of EGM signals and/or pressure signals received from IMD 14, may be performed for verifying selection of His-Purkinje pacing parameters, such as pacing electrode vector selection, pacing pulse amplitude, pacing pulse width, AV delay and/or VV delay as examples.

Figure 1B:
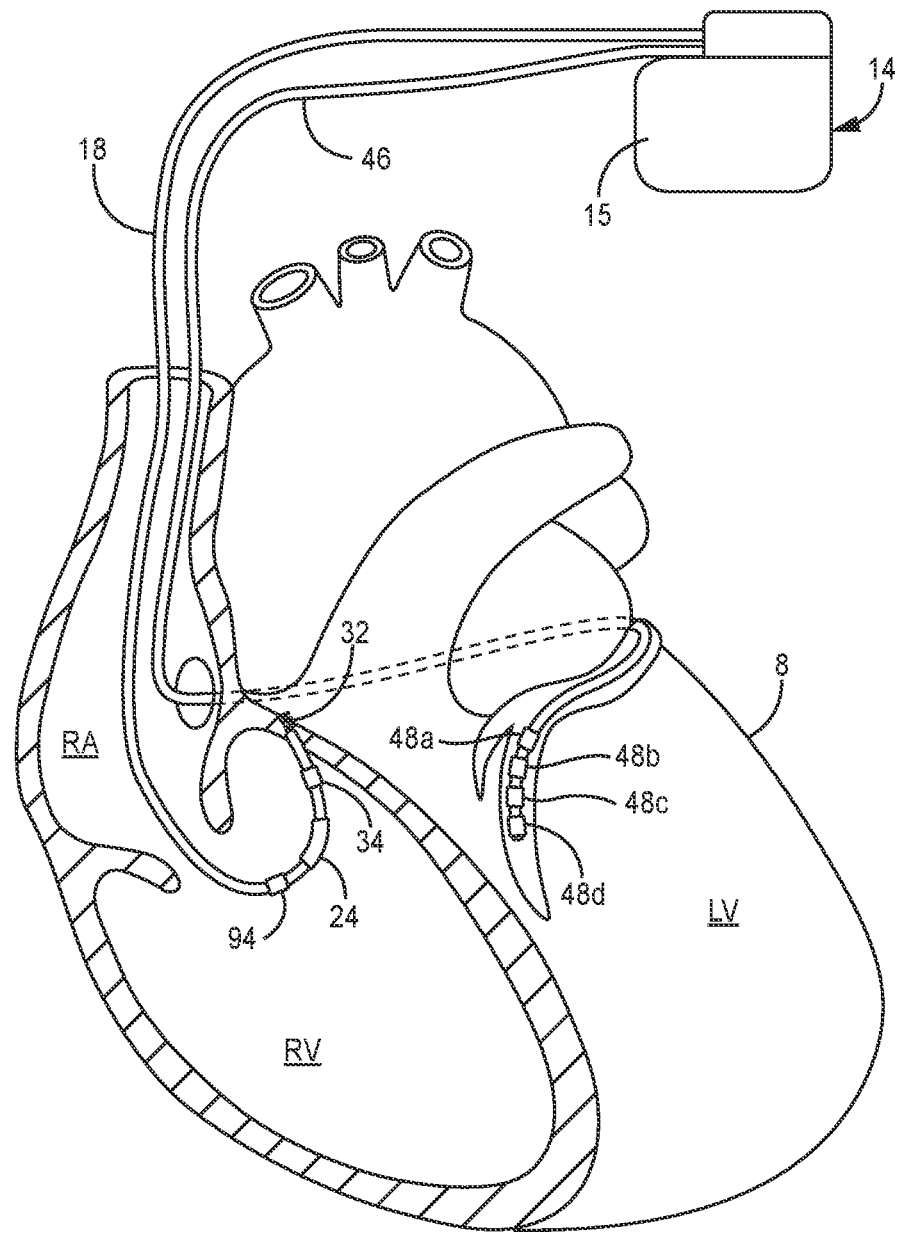
FIG. 1B is a conceptual diagram of an implantable medical device (IMD) coupled to a His-Purkinje pacing and sensing lead advanced to an alternative location in a patient's heart.

FIG. 1B is a conceptual diagram of IMD 14 coupled to His-Purkinje lead 18 advanced to an alternative location within the heart 8. In this example, the distal portion of His-Purkinje lead 18 is advanced within the RV for sensing cardiac electrical signals and delivering pacing pulses to or in the vicinity of the His bundle from a right ventricular approach. IMD 14 may be a single chamber device coupled only to His-Purkinje lead 18. In other examples, IMD 14 may be a dual chamber device and be coupled to RA lead 16 (shown in FIG. 1A) and His-Purkinje lead 18, to enable sensing of atrial P-waves and delivery of atrial pacing pulses and delivery of His-Purkinje pacing pulses at an AV delay from atrial events, sensed or paced, in an atrial synchronous pacing mode.

In this example, the tip electrode 32 of His-Purkinje pacing lead 18 is placed in the inter-ventricular septal wall, e.g., high along the inter-ventricular septal wall near the His bundle. Tip electrode 32 may be paired with the return anode ring electrode 34 for delivering His-Purkinje pacing pulses and for sensing raw cardiac electrical signals, which may be processed for obtaining a "near field" EGM signal, that may be analyzed for detecting capture type and/or for optimizing the timing of His-Purkinje pacing pulses using the techniques disclosed herein. The tip electrode 32 or the ring electrode 34 may be paired with IMD housing 15 for receiving a raw far field cardiac electrical signal that is processed to obtain a "far field" EGM signal. In some examples, a differential signal may be determined from a far field EGM signal sensed by electrodes coupled to IMD 14, which may be analyzed for determining capture type during His-Purkinje pacing according to the techniques disclosed in the above-incorporated U.S. patent application Ser. No. 17/533,005.

In this example, His-Purkinje lead 18 may carry the pressure sensor 24 for sensing a ventricular pressure signal from within the RV that may be processed and analyzed for selecting a His-Purkinje pacing control parameter, e.g., an AV delay or VV delay. In other examples, a second lead may be introduced into the RV (or LV) for carrying a pressure sensor, such as lead 17 shown in FIG. 1A, for sensing a pressure signal that is analyzed by processing circuitry included in IMD 14 (and/or external device 50, shown in FIG. 1A), for selecting at least one His-Purkinje pacing control parameter based on a feature of the pressure signal.

In the example shown, His-Purkinje lead 18 may further include an accelerometer 94 that may be carried by a distal portion of the lead body such that when electrodes 32 and 34 are positioned for delivering His-Purkinje pacing pulses, the accelerometer 94 is located within a heart chamber for sensing an acceleration signal. Processing circuitry within IMD housing 15 may receive the acceleration signal for processing and analysis. According to examples disclosed herein, the acceleration signal may be analyzed for selecting or adjusting a setting of a His-Purkinje pacing control parameter. The acceleration signal may be used for detecting the timing of atrial event signals for controlling the timing of His-Purkinje pacing pulses during an atrial synchronous ventricular pacing mode. The acceleration signal may be used for determining a patient activity metric for use in controlling a rate response ventricular pacing rate in various examples.

In some examples, His-Purkinje pacing may be delivered in combination with LV myocardial pacing that can be delivered via a coronary sinus (CS) lead 46 for further improvement in mechanical synchrony of the RV and LV, e.g., during cardiac resynchronization therapy (CRT). CS lead 46 may be advanced into the RA, through the coronary sinus ostium and into a cardiac vein of the LV for positioning electrodes 48a, 48b, 48c and 48d (collectively "CS electrodes 48") along the LV myocardium for sensing ventricular electrical signals and pacing the LV myocardium. CS lead 46 is shown as a quadripolar lead carrying four electrodes 48a-d that may be selected in various bipolar pacing electrode pairs for pacing the LV myocardial tissue and for sensing LV signals. One of CS electrodes 48 may be selected in combination with pacemaker housing 15 for delivering unipolar LV myocardial pacing in some instances and/or for sensing a far field ventricular electrical signal.

When His-Purkinje pacing lead 18 is positioned for delivering His bundle or bundle branch pacing of one or both bundle branches, His-Purkinje pacing may be combined with ventricular myocardial pacing of the LV (using CS lead 46) to correct an LV conduction delay and achieve electrical and mechanical synchrony of the ventricles. As such, in some examples, a processor of pacemaker 14 may select pacing parameters used for delivering His-Purkinje pacing pulses in combination with LV myocardial pacing, which may include an AV delay and/or an VV delay. The AV delay may control the timing of one or both of the His-Purkinje pacing pulses and the LV myocardial pacing pulses relative to an atrial event. In some examples, a VV delay may control the timing between the His-Purkinje pacing pulse delivered via His-Purkinje pacing lead 18 and the LV myocardial pacing pulse delivered via CS lead 46. As described below, processing circuitry of pacemaker 14 or external device processor 52 may receive at least one pressure signal that may be analyzed by the processing circuitry for selecting an optimal AV delay and/or VV delay based on the pressure signal analysis.

Figure 1C:
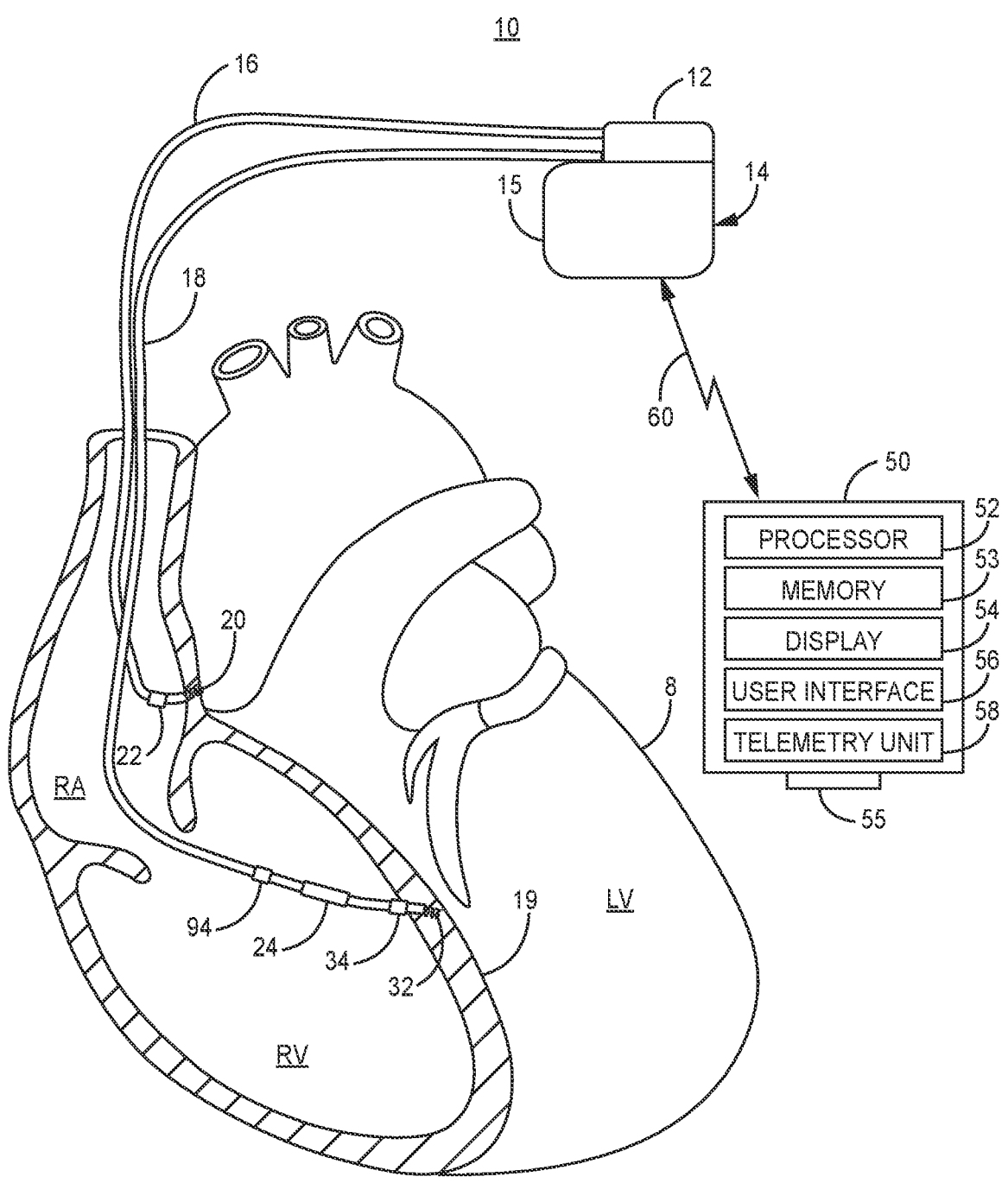
FIG. 1C is a conceptual diagram of a pacing lead coupled to the IMD of FIG. 1 in an alternative implant position for pacing the His-Purkinje system according to another example.

FIG. 1C is a conceptual diagram of pacing lead 18 coupled to IMD 14 of FIG. 1 according to an alternative implant position for pacing the His-Purkinje system. In the example shown in FIG. 1C, IMD 14 is a dual chamber device configured to receive RA lead 16, positioned in the right atrial chamber for delivering atrial pacing pulses and sensing atrial electrical signals via atrial electrodes 20 and 22. IMD 14 may be configured to sense intrinsic atrial P-waves and deliver atrial pacing pulses in the absence of sensed P-waves. IMD 14 may be configured to deliver atrial synchronized ventricular pacing by setting an AV delay in response to each sensed P-wave or atrial pacing pulse and deliver ventricular pacing pulses to the His-Purkinje system via lead 18 upon the expiration of the AV delay.

Pacing lead 18 may be advanced transvenously into the RV via the RA for positioning tip electrode 32 within the inter-ventricular septum 19. When tip electrode 32 is advanced relatively superiorly within the inter-ventricular septum 19, tip electrode 32 may be positioned along the inferior portion of the His bundle for delivering pacing pulses for capturing the His bundle or a portion thereof as described in conjunction with FIG. 1B. In FIG. 1C, tip electrode 32 may be advanced within the inter-ventricular septum 19 in the vicinity of a bundle branch of the His-Purkinje system, e.g., at a left bundle branch (LBB) pacing site or at a right bundle branch (RBB) pacing site, for delivering pacing pulses in the area of the LBB and/or RBB for capturing one or both bundle branches.

Tip electrode 32 may be selected as a pacing cathode electrode in combination with ring electrode 34 as the return anode electrode for pacing and capturing the LBB and/or RBB in various examples. In some instances, the pacing pulse amplitude and pulse width may be selected to achieve cathodal capture at the cathode electrode for capturing at least one bundle branch. In other instances, the pacing pulse amplitude and pulse width may be selected to achieve cathodal and anodal capture, which may capture both the LBB and the RBB concurrently to provide dual or bilateral bundle branch (BB) pacing using a single bipolar electrode pair. In other examples, either tip electrode 32 or ring electrode 34 may be selected as cathode electrode paired with housing 15 in a unipolar pacing electrode vector. Unipolar pacing may capture a single BB. In some cases, however, unipolar pacing may capture both the RBB and the LBB when a unipolar pacing pulse may directly capture one bundle branch while virtual current or break excitation generated by the pacing electrode may excite the other bundle branch, potentially resulting in unipolar bilateral BB pacing, with capture of both the LBB and RBB.

While pacing lead 18 is shown carrying tip electrode 32 and ring electrode 34, it is to be understood that in other examples, pacing lead 18 may include multiple electrodes along its distal portion to provide one or more selectable bipolar pacing electrode vectors and/or one or more unipolar pacing electrode vectors (with housing 15) for delivering pacing pulses to one or both of the RBB and the LBB. Other examples of His-Purkinje pacing lead configurations that may be positioned for pacing in the area of the LBB and/or RBB are generally disclosed in U.S. patent application Ser. No. 17/370,303 (Zhou, et al.) and in U.S. Publication No. 2019/0111270 (Zhou), both of which are incorporated herein by reference in its entirety.

His-Purkinje lead 18 is shown carrying pressure sensor 24 for sensing a ventricular pressure signal. As described below, one or more features of the pressure signal may be analyzed, which may be in combination with an EGM signal, for determining an optimal setting of a His-Purkinje pacing parameter. While not shown in FIGS. 1B and 1C, in some examples, a second pressure lead may be advanced to position a pressure sensor within the LV for sensing an LV pressure signal as described above in conjunction with FIG. 1A. His-Purkinje lead 18 may include an accelerometer 94 as described in conjunction with FIG. 1B. When an accelerometer 94 is carried by His-Purkinje lead 18, IMD 14 may sense atrial event signals from the acceleration signal received from accelerometer 94 for triggering His-Purkinje pacing pulses, delivered in the area of the LBB and/or RBB in this example, at an AV delay after the atrial event signal.

IMD 14 may communicate via wireless telemetry with external device 50. As described above in conjunction with FIG. 1A, external device 50 may receive EGM signals, pressure signals and/or acceleration signals from IMD 14 for processing and analysis and/or display by display unit 54 for use in selecting and programming His-Purkinje pacing control parameters.

Figure 2A:
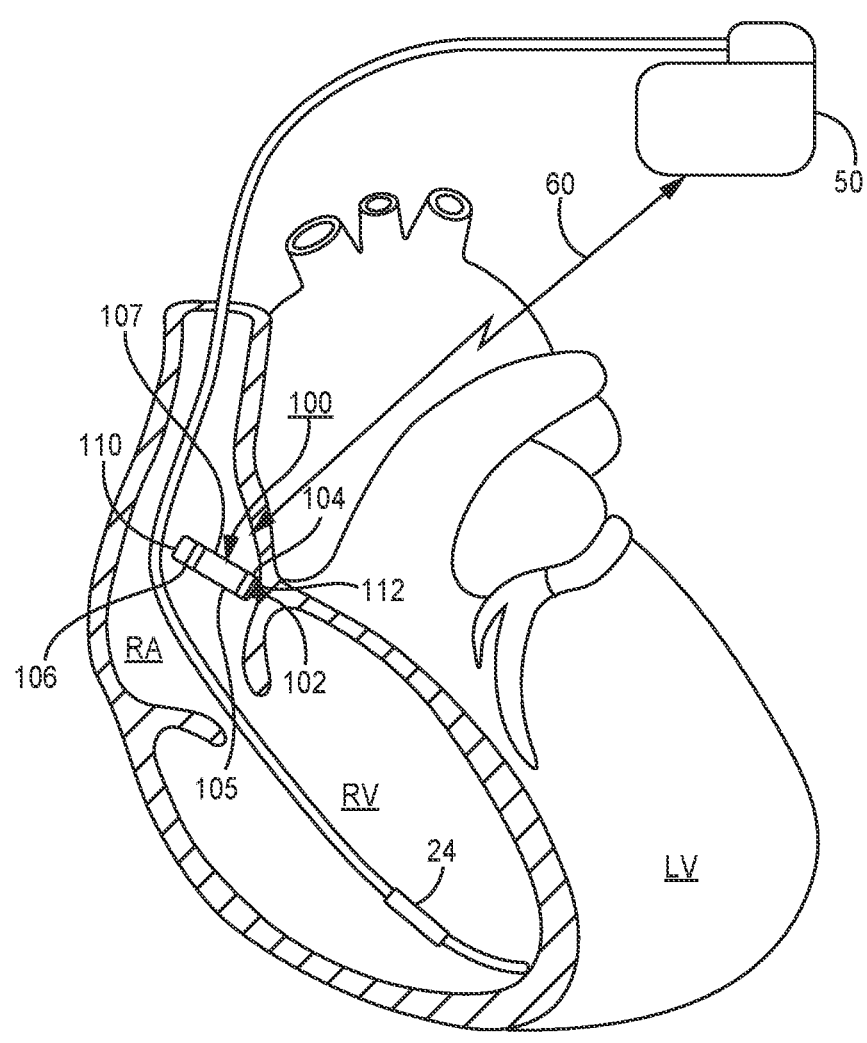
FIG. 2A is a conceptual diagram of a leadless pacemaker positioned within the right atrium for providing His-Purkinje system pacing.

FIG. 2A is a conceptual diagram of a leadless pacemaker 100 positioned within the RA for providing ventricular pacing via the His-Purkinje system. Pacemaker 100 may include a distal tip electrode 102 extending away from a distal end 112 of the pacemaker housing 105. Pacemaker 100 is shown implanted in the RA of the patient's heart to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100. Electrodes 104 and 106 are shown as ring electrodes circumscribing the longitudinal sidewall 107 of pacemaker housing 105. Longitudinal sidewall 107 extends from distal end 112 to proximal end 110. In other examples, a return anode electrode used in sensing and pacing may be positioned on housing proximal end 110. Pacing of the His-Purkinje system may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a cardiac electrical signal may be sensed using distal tip electrode 102 and distal housing-based electrode 104. A second cardiac electrical signal, which is a relatively more far-field signal, may be sensed using electrodes 104 and 106. The raw cardiac electrical signals may be processed by sensing and control circuitry included in pacemaker 100, e.g., as described below in conjunction with FIG. 3, for producing a near field His-Purkinje EGM signal and a relatively more far-field EGM signal. The EGM signals may be further processed and analyzed, in conjunction with pressure signal analysis in some examples, for determining capture and in optimizing His-Purkinje pacing parameters, such as an AV delay. In some examples, atrial P-waves may be sensed from a signal received via electrodes 104 and 106 and/or atrial pacing pulses may be delivered via electrodes 104 and 106. Atrial synchronous ventricular pacing pulses may be delivered via electrodes 102 and 104 to capture at least a portion of the His-Purkinje system at an AV delay following atrial P-waves and/or atrial pacing pulses.

In the example of FIG. 2A, a pressure lead 17 is advanced in the RV to position pressure sensor 24 for sensing a ventricular pressure signal. In this configuration, pressure lead 17 may be connected to an external device, e.g., external device 50, that receives the pressure signal for display, processing and analysis. Pacemaker 100 may transmit EGM signals to external device 50 for processing and analysis by external device processor 52 (shown in FIG. 1A). Based on the analysis of cardiac electrical signals (which may include one or more ECG signals and/or EGM signals) and the ventricular pressure signal received by external device 50, external device processing circuitry may determine one or more His-Purkinje pacing parameters for use by pacemaker 100 in delivering His-Purkinje pacing pulses for promoting optimal electrical and/or mechanical synchrony of the heart chambers.

In some examples, e.g., as shown in FIGS. 1A and 1B, the pressure sensor 24 may be carried by a lead 17 that may remain implanted in the patient chronically for providing a pressure signal to IMD 14 for setting and adjusting one or more His-Purkinje pacing parameters to optimize hemodynamic performance of heart 8 based on at least one feature of the sensed pressure signal. In other examples, e.g., in the configuration of FIG. 2A, pressure sensor 24 may be carried by a temporary sensing wire or lead that may be removed after sensing pressure signals and selecting and programming His-Purkinje pacing parameters. As described in conjunction with FIG. 1A, a temporary pressure lead may be advanced within the RV, within the LV or within both the RV and the LV at the time of pacemaker 100 implant or during a follow-up procedure for performing an optimization process for selecting His-Purkinje pacing control parameters for improving the mechanical synchrony of the heart chambers. A lead carrying a pressure sensor may be configured for coupling to external device 50 or to a dedicated pressure monitor that may transmit the pressure signal or associated data to a computer or external device 50 for processing and analysis according to the techniques disclosed herein.

Figure 2B:
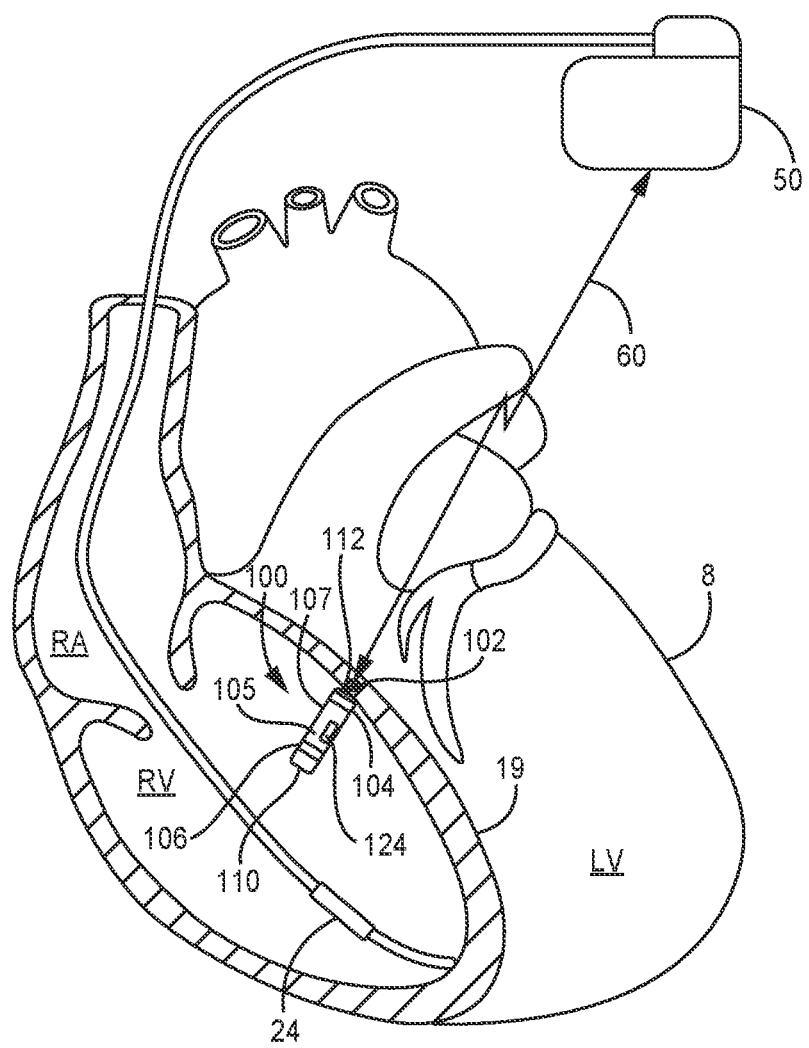
FIG. 2B is a conceptual diagram of a leadless pacemaker positioned within the right ventricle for providing His-Purkinje system pacing.

FIG. 2B is a conceptual diagram of the leadless pacemaker 100 of FIG. 2A shown implanted in an alternative location for pacing the His-Purkinje system. Pacemaker 100 may be implanted within the RV along the inter-ventricular septum 19 for providing His-Purkinje system pacing in some examples. Techniques disclosed herein may be used in conjunction with a leadless pacemaker, such as pacemaker 100, having a pacing electrode coupled to and extending from the pacemaker housing 105, without requiring an intervening medical lead coupled to the pacemaker for carrying the pacing and sensing electrode(s).

In this example, pacemaker 100 may be positioned within the RV for advancing the pacing tip electrode 102 extending from the distal end 112 of pacemaker housing 105 into the inter-ventricular septum 19 for pacing the His-Purkinje system, e.g., in the area of inferior portion of the His bundle or along one or both of the RBB and LBB. Tip electrode 102 is shown as a "screw-in" helical electrode but may be configured as other types of electrodes capable of being advanced within the septal tissue. A proximal portion of the pacing tip electrode 102 may be electrically insulated, e.g., with a coating, in some examples such that only a distal portion of tip electrode 102, furthest from pacemaker housing distal end 112, is exposed to provide targeted pacing at a tissue site that includes the His bundle, LBB or RBB.

In other examples, tip electrode 102 may be formed having a straight shaft with a distal active electrode portion or other type of electrode that is advanceable through the inter-ventricular septum 19 to deliver pacing, e.g., in a left portion of the septum 19 in the area of the LBB. In some examples, pacemaker 100 may include a fixation member that includes one or more tines, hooks, barbs, helices or other fixation member(s) that anchor the distal end 112 of the pacemaker 100 at the implant site and may not function as an electrode. Examples of leadless intracardiac pacemakers that may be configured for delivering cardiac pacing pulses to the His-Purkinje system that may be used in conjunction with the techniques described herein are generally disclosed in U.S. Publication No. 2019/0111270 (Zhou) and U.S. Publication No. 2019/0083800 (Yang, et al.), both of which are incorporated herein by reference in their entirety.

Pacemaker 100 may include the distal housing-based ring electrode 104 along or near the distal end 102 of pacemaker housing 105. Distal housing-based ring electrode 104 may be selectable as the return anode electrode with tip electrode 102 for bipolar pacing of the LBB or RBB in the vicinity of the tip electrode 102. Bipolar bilateral BB pacing of both the RBB and LBB simultaneously may be achieved by cathodal capture of the LBB at tip electrode 102 and anodal capture of the RBB by distal ring electrode 104. The polarities of the tip electrode 102 and the distal ring electrode 104 may be reversed to achieve cathodal capture of the RBB and anodal capture of the LBB in some examples. Distal ring electrode 104 is shown as a ring electrode circumscribing a distal portion of the housing 105 but may alternatively be a distal housing-based electrode in the form of a button electrode, hemispherical electrode, segmented electrode or the like and may be along the face of distal end 112 of housing 105 and/or along longitudinal sidewall 107.

In the example shown, a housing-based proximal ring electrode 106, which may circumscribe all or a portion of the longitudinal sidewall 107 of the housing 105, may be provided as a return anode electrode. In other examples, a return anode electrode used in sensing and pacing may be positioned on housing proximal end 110 and may be a button, ring or other type of electrode. Pacing of the LBB may be achieved using the tip electrode 102 as the cathode electrode and the proximal ring electrode 106 as the return anode. Pacing of the RBB may be achieved using the distal ring electrode 104 as a cathode electrode and the proximal ring electrode 106 as the return anode. In this way, bilateral or dual bundle branch pacing may be achieved using two different bipolar pacing electrode vectors carried by housing 105.

Cardiac electrical signals produced by heart 8 may be sensed by pacemaker 100 using electrodes 102, 104 and/or 106. The cardiac electrical signal received via electrodes 102 and 104, electrodes 104 and 106 and/or electrodes 102 and 106, for example. The cardiac electrical signals sensed by pacemaker 100 may be processed and transmitted wirelessly, e.g., as EGM signals, to external device 50 via communication link 60 in some examples. The signals may then be displayed and/or further processed and analyzed by the processor 52 of external device 50 for providing a user with visual information regarding pacing pulse output levels that result in a change in the type of capture (or loss of capture) of the His-Purkinje system and/or changes in electrical synchrony of the ventricular chambers associated with changes in AV delay.

As described above in conjunction with FIG. 2A, a pressure sensor 24 may be carried by a temporary sensing wire or lead 17 that may be removed after sensing pressure signals and selecting and programming His-Purkinje pacing parameters. A lead 17 carrying a pressure sensor 24 may be configured for coupling to external device 50 or to a dedicated pressure monitor that may transmit the pressure signal or associated data to a computer or external device 50 for display to a user and/or for processing and analysis according to the techniques disclosed herein for selecting His-Purkinje pacing parameters.

In other examples, pacemaker 100 may include a pressure sensor 124 which may be in or on housing 105 and exposed to surrounding blood pressure via a window in housing 105. Examples of a leadless pacemaker including a pressure sensor are generally disclosed in U.S. Publication No. 2018/0021567 (An, et al.) and in U.S. Publication No. 2020/0316386 (Demmer, et al.), incorporated herein by reference in their entirety.

The examples of FIGS. 1A-2B present various lead and/or electrode configurations that may be implemented for delivering His-Purkinje pacing in a system configured to perform the techniques disclosed herein for sensing cardiac electrical signals and at least one pressure signal analyzed for use in selecting and adjusting pacing parameters used in controlling His-Purkinje pacing. As described below, an optimized pacing parameter setting, such as a pacing delay interval which may be an AV delay or VV delay, may be identified based on analysis of a pressure signal, which may be analyzed in combination with a cardiac electrical signal in some examples. The particular lead and electrode configurations described and shown in the accompanying drawings are intended to be illustrative in nature. It is to be understood that the leads and electrodes illustrated in FIGS. 1A-2B may be implanted in different combinations than the example combinations shown. For example, the CS lead 46 as shown in FIG. 1B may be combined with the leadless pacemaker 100 shown in FIGS. 2A and 2B for delivering His-Purkinje pacing in combination with LV myocardial pacing. In other examples, the RA lead 16, e.g., as shown in FIG. 1A, may or may not be included in any of the example configurations shown in FIGS. 1A-2B. A variety of lead-based and leadless electrode and sensor configurations may be conceived for sensing cardiac electrical signals, sensing at least one pressure signal, and delivering pacing pulses to the His-Purkinje system in accordance with the techniques disclosed herein.

Figure 3:
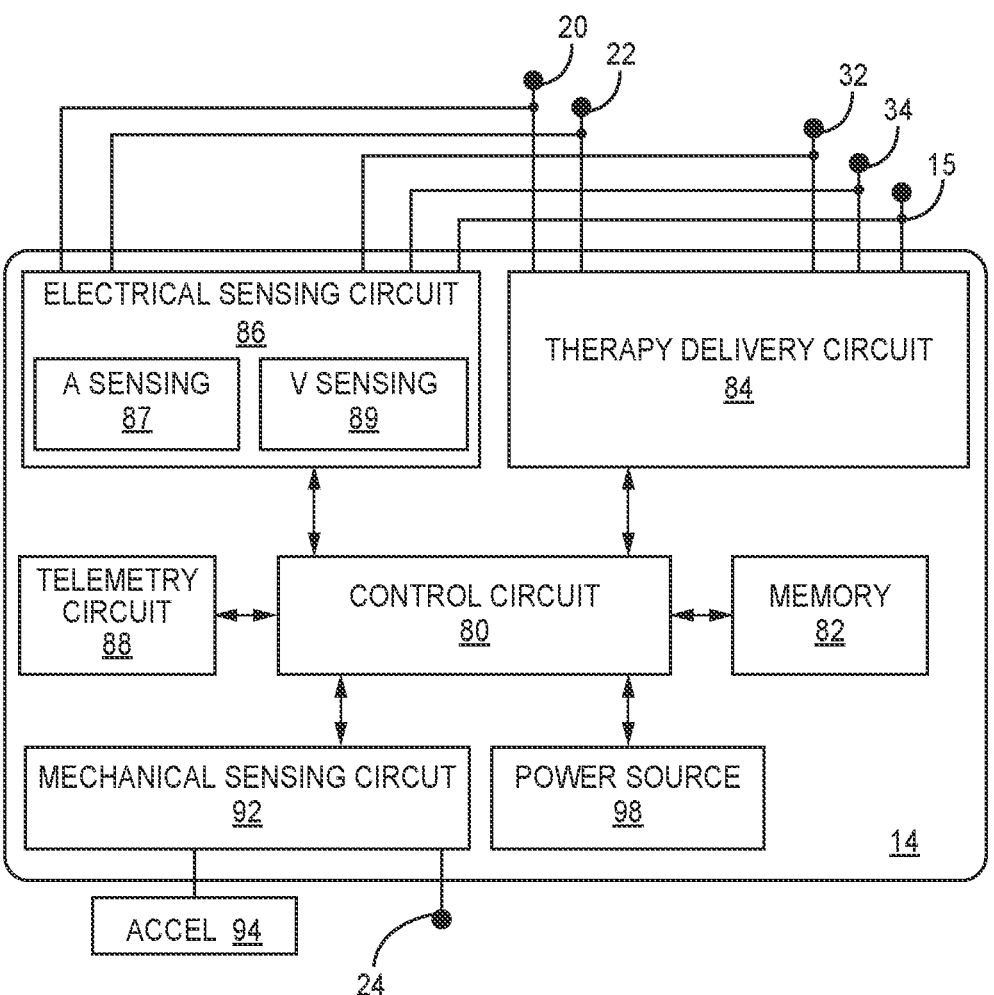
FIG. 3 is a schematic diagram of circuitry that may be enclosed within a medical device configured to perform His-Purkinje system pacing according to the techniques disclosed herein.

FIG. 3 is a schematic diagram of circuitry that may be enclosed within a medical device configured to perform His-Purkinje pacing according to the techniques disclosed herein. The block diagram of FIG. 3 is described with reference to IMD 14 coupled to electrodes carried by RA lead 16 and His-Purkinje lead 18 including pressure sensor 24 as shown in FIG. 1C for the sake of illustration. It is to be understood, however, that the functionality attributed to the various circuits and components shown in FIG. 3 for controlling and delivering His-Purkinje pacing may be implemented in conjunction with other lead and electrode configurations, including the leadless pacemaker 100 of FIGS. 2A and 2B or other medical devices configured to deliver His-Purkinje pacing pulses and sense cardiac electrical signals and ventricular pressure signals.

Housing 15 is represented as an electrode in FIG. 3 for use in cardiac electrical signal sensing and, in some examples, for delivery of cardiac electrical stimulation pulses such as unipolar pacing pulses. The electronic circuitry enclosed within housing 15 includes software, firmware and hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, cardiac electrical signal sensing circuit 86, telemetry circuit 88, mechanical signal sensing circuit 92 and power source 98.

Power source 98 provides power to the circuitry of IMD 14 including each of the components 80, 82, 84, 86, 88, and 92 as needed. Power source 98 may include one or more energy storage devices, such as one or more rechargeable or non-rechargeable batteries. The connections between power source 98 and each of the other components 80, 82, 84, 86, 88 and 92 are to be understood from the general block diagram of FIG. 3 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc. as needed for sensing cardiac electrical signals, and to mechanical signal sensing circuit 92 for enabling pressure sensor 24 for sensing a pressure signal that is passed to control circuit 80. Power source 98 may provide power to the various components and circuits of telemetry circuit 88 and memory 82 as needed, which may be under the control of control circuit 80.

The functional blocks shown in FIG. 3 represent functionality included in IMD 14 and may include any discrete and/or integrated electronic circuit components that implement analog and/or digital circuits capable of producing the functions attributed to IMD 14 (or pacemaker 100) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for cooperatively sensing cardiac electrical signals and controlling delivery of cardiac electrical stimulation therapies in response to sensed cardiac events, e.g., P-waves attendant to atrial depolarizations and R-waves attendant to ventricular depolarizations, or the absence thereof. The available electrodes are electrically coupled to therapy delivery circuit 84 for delivering electrical stimulation pulses and/or to sensing circuit 86 for sensing cardiac electrical signals produced by the heart, which may include both intrinsic signals (such as intrinsic R-waves) produced by the heart in the absence of a pacing pulse that captures the heart and evoked response signals following a delivered pacing pulse of sufficient energy to cause capture.

Sensing circuit 86 may include two or more sensing channels for sensing raw cardiac electrical signals from two or more sensing electrode vectors. For example, a RA signal may be sensed using electrodes 20 and 22 coupled to atrial sensing (A sensing) channel 87. A ventricular signal may be sensed by ventricular sensing (V sensing) channel 89 using electrodes 32 and 34. In some examples, sensing circuit 86 may include multiple sensing channels to enable sensing a raw near field His-Purkinje signal by one sensing channel, for example using electrodes 32 and 34 of His-Purkinje lead 18 and sensing a raw far field signal by another sensing channel, using a second electrode vector having electrodes spaced further apart than the electrodes of the near field sensing electrode vector, e.g., using His-Purkinje lead tip electrode 32 or ring electrode 34 paired with IMD housing 15.

As used herein, a "near field" signal refers to a cardiac electrical signal received from a sensing electrode vector including at least one electrode positioned at or proximate to the His bundle, at or in the vicinity of the site of His pacing pulse delivery, such that the near field signal may also be referred to as a "near field His-Purkinje signal." As used herein, a "far field" signal refers to a cardiac electrical signal received from a sensing electrode vector that is relatively further away from the His-Purkinje system than the electrode vector used to sense the raw near field His-Purkinje signal and/or has a greater inter-electrode distance between the two electrodes defining the far field sensing electrode vector than the inter-electrode distance between the two electrodes defining the near field His-Purkinje sensing electrode vector. A far field cardiac electrical signal produced from the raw far field signal by sensing circuit 86 may be more representative of the global activation of the ventricles as opposed to the near field signal being more representative of local tissue activation at or near the pacing site. The far field cardiac electrical signal may include an evoked response signal associated with SHP capture, NSHP capture or VM capture. Examples of differences in the evoked response signals of the near field and far field cardiac electrical signals during different capture types that may be determined and used by control circuit 80 for discriminating between capture types and selecting pacing pulse output (e.g., pacing pulse amplitude and pacing pulse width) are generally described in the above-incorporated U.S. patent application Ser. No. 17/533,005 (Cao, et al.).

Sensing circuit 86 may include switching circuitry for selectively coupling a sensing electrode pair from the available electrodes a respective sensing channel. Switching circuitry may include a switch array, switch matrix, multiplexer, or any other type of switching device suitable to selectively couple components of sensing circuit 86 to selected electrodes.

Each of sensing channels 87 and 89 may include an input filter for receiving a raw cardiac electrical signal from a respective pair of sensing electrodes, a pre-amplifier, an analog-to-digital converter and a bandpass filter for producing a multi-bit digital cardiac electrical signal, which may be referred to as an "EGM" signal when the raw signal is sensed from within a heart chamber. In some examples, features of the post-pace far field cardiac electrical signal and/or near field His-Purkinje signal following a His-Purkinje pacing pulse may be used to select His-Purkinje pacing control parameters. The post-pace signal following a His-Purkinje pacing pulse that captures the His-Purkinje system and/or the ventricular myocardium may also be referred to herein as an "evoked response signal" that is attendant to the pacing-evoked depolarizations caused by the pacing pulse, which may be sensed by sensing circuit 86.

Each sensing channel 87 and 89 may include cardiac event detection circuitry, which may include one or more sense amplifiers, filters, rectifiers, threshold detectors, comparators, analog-to-digital converters (ADCs), timers or other analog or digital components, for detecting cardiac electrical events. For example, an atrial event detector may be included in A sensing channel 87 for detecting intrinsic P-waves attendant to intrinsic atrial depolarizations using one or both of electrodes 20 and 22 carried by RA lead 16. A ventricular event detector may be included in V sensing channel 89 for detecting intrinsic R-waves attendant to intrinsic ventricular depolarizations using electrodes 32 and 34 carried by His-Purkinje lead 18.

A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86. The R-wave sensing threshold, for example, may be controlled to start at a starting threshold voltage following a post-ventricular blanking period then decrease according to a decay profile until reaching a minimum sensing threshold. The minimum R-wave sensing threshold may be set to a programmed sensitivity of the R-wave detection circuitry. The sensitivity, programmed to a voltage level typically in millivolts, is the lowest voltage level above which a cardiac event, e.g., a P-wave or an R-wave, can be sensed by the cardiac event detection circuitry of the respective A sensing channel 87 or V sensing channel 89.

Upon detecting a cardiac electrical event based on a sensing threshold crossing, sensing circuit 86 may produce a sensed event signal that is passed to control circuit 80. For example, an atrial event detector may produce a P-wave sensed event signal in response to a P-wave sensing threshold crossing. A ventricular event detector may produce an R-wave sensed event signal in response to an R-wave sensing threshold crossing. The sensed event signals can be used by control circuit 80 for setting pacing escape interval timers that control the basic time intervals used for scheduling cardiac pacing pulses. Control circuit 80 may include various timers or counters for counting down an AV delay, a VV delay, an atrial lower rate interval, a ventricular lower rate interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a His-Purkinje pacing pulse at the selected AV delay. If the AV delay expires before control circuit 80 receives an R-wave sensed event signal from sensing circuit 86, therapy delivery circuit 84 may generate and deliver a His-Purkinje pacing pulse at the AV delay following the sensed P-wave and in this way deliver atrial-synchronized ventricular pacing. If an R-wave sensed event signal is received from sensing circuit 86 before the AV delay expires, the scheduled His-Purkinje pacing pulse may be inhibited. The AV delay controls the amount of time between an atrial event, paced or sensed, and a His-Purkinje pacing pulse to promote electrical and mechanical synchrony of the heart chambers.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to the therapy delivery circuit 84. Therapy delivery circuit 84 may include one or more pacing channels. In the example of IMD 14, therapy delivery circuit 84 may include an atrial pacing channel and a ventricular pacing channel each including one or more holding capacitors, one or more switches, and an output capacitor for producing pacing pulses delivered by the respective RA lead 16 (e.g., via electrodes 20 and 22) or His-Purkinje lead 18 (e.g., via electrodes 32 and 34).

Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber and/or dual chamber pacing modes, cardiac resynchronization therapy (CRT) or anti-tachycardia pacing sequences. The microprocessor of control circuit 80 may also set the amplitude, pulse width, polarity or other characteristics of the cardiac pacing pulses, which may be based on programmed values stored in memory 82.

In some examples, IMD 14 may be configured to detect non-sinus tachycardia and deliver anti-tachycardia pacing (ATP). When IMD 14 is configured to detect tachyarrhythmia and deliver CV/DF shocks, therapy delivery circuit 84 may include high voltage therapy circuitry for generating high voltage shock pulses in addition to low voltage therapy circuitry for generating low voltage pacing pulses. In response to detecting atrial or ventricular tachycardia or fibrillation, control circuit 80 may control therapy delivery circuit 84 to deliver a CV/DF shock. The high voltage therapy circuitry may include high voltage capacitors and high voltage charging circuitry for generating and delivering CV/DF shock pulses using coil electrodes carried by one or more leads coupled to IMD 14 and/or housing 15.

Control parameters utilized by control circuit 80 for sensing cardiac events and controlling pacing therapy delivery may be programmed into memory 82 via telemetry circuit 88. Telemetry circuit 88 includes a transceiver and antenna for communicating with an external device 50 (FIG. 1A) using radio frequency communication or other communication protocols as described above. Under the control of control circuit 80, telemetry circuit 88 may receive downlink telemetry from and send uplink telemetry to the external device 50. In some cases, telemetry circuit 88 may be used to transmit and receive communication signals to/from another medical device implanted in the patient.

Mechanical sensing circuit 92 may receive a pressure signal from pressure sensor 24 and pass the pressure signal, which may be filtered, amplified and digitized by mechanical sensing circuit 92. Mechanical sensing circuit 92 may be configured to determine a derivative signal or first order difference signal for passing a dP/dt signal to control circuit 80 in some examples. For instance, mechanical sensing circuit 92 may include a hardware, firmware or software based differentiator or difference filter for producing a first order difference signal that is passed to control circuit 80. In other examples, control circuit 80 may receive the pressure signal from mechanical sensing circuit 92 and process the pressure signal by hardware, firmware and/or software based processing circuitry for filtering, amplifying, rectifying and/or producing a difference signal from which pressure signal features may be determined. As described below, control circuit 80 may analyze the pressure signal(s) for determining an optimal His-Purkinje pacing control parameter for promoting mechanical synchrony and optimized hemodynamic performance of the heart chambers.

In some examples, mechanical sensing circuit 92 may include an accelerometer 94 for sensing an acceleration signal. The accelerometer 94 may be a single axis or multi-axis accelerometer that may be carried by a lead extending within the RA, RV or LV. In the case of leadless pacemaker 100, the accelerometer 94 may be enclosed within the housing 105 for sensing cardiac acceleration signals from within the heart. The acceleration signal may be used for determining a patient activity level for controlling rate responsive pacing in some examples. The acceleration signal may include atrial event signals that may be sensed by control circuit 80 for setting an AV delay for controlling the timing of His-Purkinje pacing pulses. In some examples, the morphology of a ventricular event signal may be determined from the acceleration signal during His-Purkinje pacing at an AV delay that has been optimized based on analysis of the pressure signal. Control circuit 80 may detect a change in the morphology of the ventricular event acceleration signal as an indicator of a change in the electromechanical synchrony and a need to adjust the AV delay to restore more optimal heart chamber synchrony. The acceleration signal may additionally or alternatively be used by control circuit 80 for determining a patient physical activity metric, sometimes referred to as an "activity count," for adjusting the pacing mode and/or ventricular pacing rate to provide rate responsive pacing. During rate responsive pacing, the ventricular pacing rate may be increased to provide rate support during increased physical activity of the patient.

Figure 4:
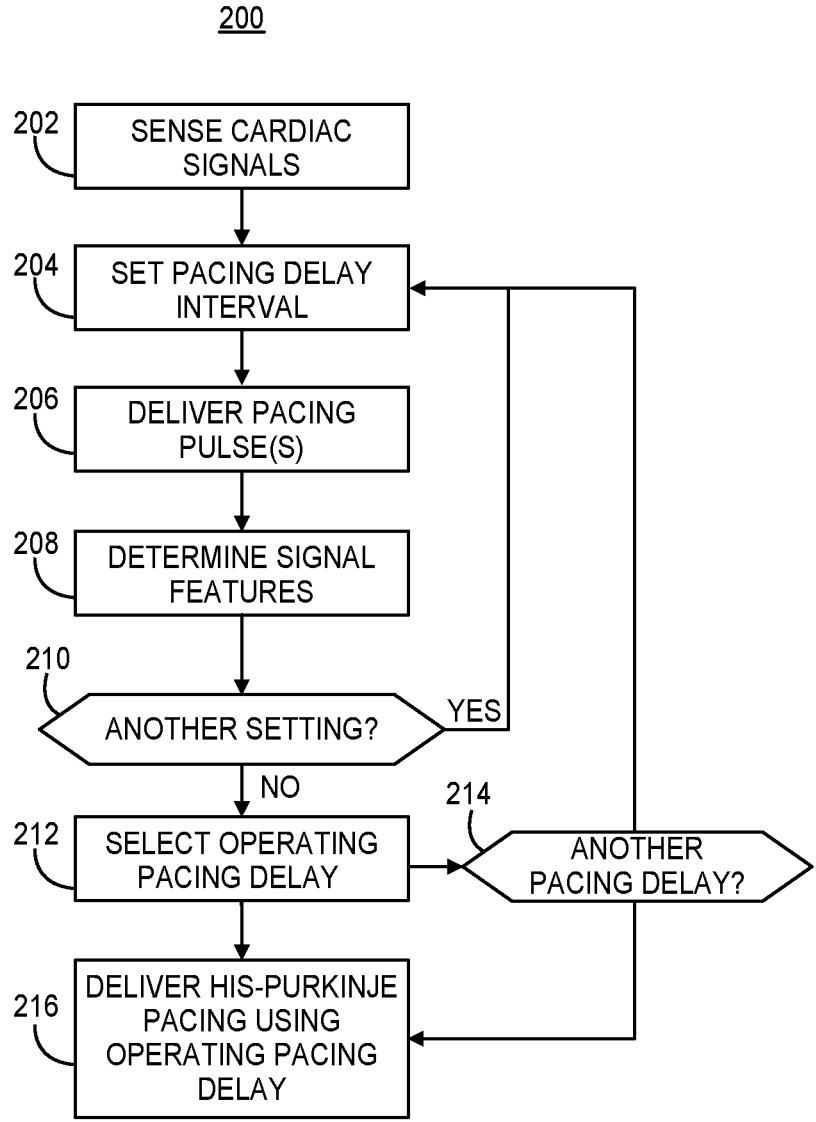
FIG. 4 is a flow chart of a method for selecting a His-Purkinje pacing parameter according to one example.

FIG. 4 is a flow chart 200 of a method for selecting a His-Purkinje pacing parameter based on analysis of a cardiac mechanical signal according to one example. For the sake of convenience, the process of flow chart 200 is described as being performed by circuitry of IMD 14 coupled to electrodes 20, 22, 32 and 34 and pressure sensor 24. It is to be understood, however, that the techniques described in conjunction with flow chart 200 and other flow charts and diagrams presented herein may be performed by processing circuitry of pacemaker 100, external device 50, or another medical device configured to receive a cardiac mechanical signal, e.g., a ventricular pressure signal, following the delivery of one or more ventricular pacing pulses delivered for capturing at least a portion of the His-Purkinje system. Processing and analysis of cardiac electrical and mechanical signals may be performed cooperatively by processing circuitry included in two or more medical devices in communication with each other, e.g., IMD 14 (or pacemaker 100) and external device 50 in some examples. For instance, when a temporary pressure lead is positioned in the RV and/or LV and the corresponding pressure signal(s) is(are) received by external device 50, external device 50 may additionally receive EGM signals and/or marker channel signals from IMD 14 (or pacemaker 100) indicating the timing of sensed cardiac event signals and His-Purkinje pacing pulses. External device processor 52 may perform signal analysis described in conjunction with flow chart 200 for selecting a His-Purkinje pacing parameter that can be programmed in IMD 14 (or pacemaker 100).

At block 202, sensing circuit 86 of IMD 14 senses cardiac electrical signals using sensing electrode vectors selected from electrodes 20, 22, 32 and 34 and housing 15. Sensing circuit 86 may sense an atrial electrical signal for sensing intrinsic P-waves for triggering atrial synchronous His-Purkinje pacing pulses. Sensing circuit 86 senses a ventricular electrical signal for sensing intrinsic R-waves for inhibiting a His-Purkinje pacing pulse in response to a sensed R-wave.

In addition to cardiac electrical signals, mechanical sensing circuit 92 may sense a pressure signal via pressure sensor 24 at block 202. In some examples, an RV pressure signal is sensed via a pressure sensor 24 positioned within the RV. In other examples, pressure sensor 24 may be advanced within the LV for sensing an LV pressure signal. In still other examples, two pressure sensors may be advanced within the patient's heart, one in the RV and one in the LV, for sensing both an RV pressure signal and an LV pressure signal. As described above, mechanical sensing circuit 92 may sense an acceleration signal by an accelerometer in some examples.

At block 204, control circuit 80 may set an initial test setting of a pacing delay interval. Control circuit 80 controls therapy delivery circuit 84 to deliver His-Purkinje pacing pulses at block 206 according to the test pacing delay. In some examples, the pacing delay interval is an AV delay that is started in response to identifying atrial events, which may be sensed P-waves and/or delivered atrial pacing pulses. Control circuit 80 may receive a P-wave sensed event signal from sensing circuit 85 and start the AV delay in response to the received P-wave sensed event signal. When a P-wave is not received before a lower rate pacing interval expires, e.g., an atrial lower rate interval corresponding to a minimum atrial rate of 40 to 60 beats per minute, therapy delivery circuit 84 may deliver an atrial pacing pulse. Control circuit 80 may start the AV delay in response to the delivered atrial pacing pulse.

In order to avoid beat-to-beat variation due to intermittent atrial pacing during the process of flow chart 200, control circuit 80 may control therapy delivery circuit 84 to deliver atrial pacing pulses at a rate that is faster than the intrinsic atrial rate in some examples. In this way, all AV delay intervals may be started in response to a delivered atrial pacing pulse. In other examples, control circuit 80 may set the atrial lower rate to a minimum rate or set the pacing mode to withhold atrial pacing such that all AV delay intervals are started in response to a P-wave sensed event signal.

In other examples, the pacing delay interval set to a test setting at block 204 may be a VV delay for controlling the timing of a His-Purkinje pacing pulse relative to another ventricular pacing pulse, e.g., delivered to the LV myocardium via CS lead 46 shown in FIG. 1B. Therapy delivery circuit 84 may deliver each His-Purkinje pacing pulse and LV myocardial pacing pulse at block 206 according to the VV delay setting. In some examples, therapy delivery circuit 84 delivers the His-Purkinje pacing pulse at the VV delay interval from the ventricular myocardial pacing pulse. In other examples, the His-Purkinje pacing pulse may be delivered at a ventricular lower rate interval or upon expiration of an AV delay. The VV delay may be started in response to delivery of the His-Purkinje pacing pulse, and the ventricular myocardial pacing pulse may be delivered upon expiration of the VV delay. In still other examples, the ventricular myocardial pacing pulse may be delivered first, either upon expiration of an AV delay or expiration of a ventricular lower rate interval (which may be a temporary rate response interval during patient physical activity), and the His-Purkinje pacing pulse may be delivered upon expiration of the VV delay interval after the ventricular myocardial pacing pulse. It is to be understood that the VV delay can be set to 0 ms such that a His-Purkinje pacing pulse and a ventricular myocardial pacing pulse are delivered simultaneously.

At block 208, control circuit 80 determines one or more features of the ventricular pressure signal(s) and/or acceleration signal following each of one or more His-Purkinje pacing pulses delivered according to the test pacing delay interval at block 206. The maximum peak amplitude, maximum positive and/or negative dP/dt (slope), signal width, area of the pressure signal waveform and/or the waveform morphology matching score relative to a previously established waveform template may be determined, as examples. In some examples, an electromechanical time delay may be determined as the time interval from a ventricular electrical event identified by control circuit 80 to a fiducial point of the pressure signal. The electromechanical time delay may be determined by control circuit 80 as the time of a fiducial point of the pressure signal relative to a preceding electrical event, e.g., relative to the delivered His-Purkinje pacing pulse or relative to a maximum peak of the pacing-evoked QRS signal, a threshold crossing time of the pacing-evoked QRS signal or another reference time point of a ventricular electrical event that immediately precedes the ventricular pressure waveform. For example, an electromechanical time delay may be determined as the time interval from an identified ventricular electrical event to the maximum dP/dt, also referred to herein as the "maximum slope" of the RV pressure signal and/or the maximum dP/dt of the LV pressure signal. The determined pressure signal features, which may include an electromechanical time delay, may be stored in memory 82 with the associated pacing delay setting.

Additionally or alternatively, a mechanical delay time between a point of a first signal and a point of a second signal sensed by the mechanical sensing circuit 92 may be determined. For instance, when an RV pressure signal is being sensed and an LV pressure signal is being sensed, a mechanical delay time between the RV maximum dP/dt and the LV maximum dP/dt may be determined as an inter-ventricular mechanical delay time by control circuit 80.

In still other examples, the electromechanical time delay may be determined from the identified ventricular electrical event to a fiducial point of a sensed acceleration signal. Control circuit 80 may determine the electromechanical time delay as the time interval from a His-Purkinje pacing pulse or maximum peak of a QRS waveform to the subsequent maximum peak amplitude of the acceleration signal or the maximum slope of the acceleration signal. A mechanical delay time may be determined between a point on the pressure signal and a point on the acceleration signal sensed by mechanical sensing circuit 92. For instance, a mechanical delay time may be determined between the time of the maximum peak amplitude of the acceleration signal and the time of the maximum dP/dt of the RV or LV pressure signal. As an example, when an accelerometer is positioned in the RV for sensing an acceleration signal and a pressure sensor is positioned in the LV for sensing a pressure signal, a mechanical delay time may be determined between a fidu-cial point (maximum peak, maximum slope, etc.) of the acceleration signal and a fiducial point of the pressure signal during a ventricular beat or cycle following a His-Purkinje pacing pulse.

In some examples, control circuit 80 may determine one or more features of a sensed ventricular electrical signal at block 208. One or more features may be determined from a near field signal sensed relatively locally at the His-Purkinje pacing site, e.g., sensed using electrodes 32 and 34. Addi-tionally or alternatively, one or more features may be determined from a relatively more global far field signal, e.g., sensed using electrode 32 or electrode 34 paired with IMD housing 15. The sensed electrical signals may be used by control circuit 80 to verify capture. In some examples, the sensed electrical signals may be used for determining the electromechanical time delay, e.g., from a QRS signal peak to a maximum peak pressure or maximum dP/dt as described above. In still other examples, the sensed electrical signals may be analyzed for determining features that may be used in combination with the pressure signal feature(s) and/or acceleration signal features for selecting an operating pacing delay interval. For example, QRS width may be determined from a far field EGM signal for verifying an improvement in electrical synchrony of the ventricular chambers and evi-dence of capture of the His-Purkinje system. The electro-mechanical time delay may be used for selecting an oper-ating pacing delay interval once effective capture of at least a portion of the His-Purkinje system is determined based on the cardiac electrical signal(s).

Control circuit 80 may determine whether additional test pacing delay interval settings are available at block 210. Control circuit 80 may be configured to control therapy delivery circuit 84 to deliver His-Purkinje pacing pulses at each of multiple AV delay settings and/or VV delay settings to enable control circuit 80 to assess the optimal operating AV delay and/or operating VV delay for achieving improved synchrony of the heart chambers based on analysis of at least one cardiac mechanical signal, e.g., a pressure signal and/or acceleration signal sensed by mechanical sensing circuit 92. When additional pacing delay interval settings are available, as determined at block 210, control circuit 80 may return to block 204 to set the pacing delay interval to a different test setting and repeat the process of blocks 206 and 208. For example, control circuit 80 may apply AV delay settings ranging from 30 ms to 200 ms or from 50 ms to 150 ms as examples. One, two, three, four, six, eight or more AV delay test settings may be applied.

Additionally or alternatively, control circuit 80 may apply VV delay settings ranging from −50 to +50, −80 to +80 ms, or −100 to +100 ms, as examples, where a negative VV delay may indicate that a ventricular pacing pulse being delivered to a second pacing site is delivered earlier than a His-Purkinje pacing pulse delivered to a first ventricular pacing site along the His-Purkinje conduction system. The second pacing site may be a myocardial pacing site, e.g., the LV myocardium via a CS lead, or another His-Purkinje pacing site. For example, His-Purkinje pacing pulses may be delivered to a first pacing site along or in the area of the His bundle and to a second pacing site along or in the area of a bundle branch. The two His-Purkinje pacing pulses deliv-ered to two different His-Purkinje pacing sites may be separated in time by the VV delay. A VV delay may control a time interval between a LBB pacing pulse and a RBB pacing pulse in another example. Two or more VV delay settings may be applied during the process of flow chart 200 for enabling control circuit 80 to select an operating VV delay setting based on cardiac mechanical signal features, which may include the electromechanical time delay and/or inter-ventricular mechanical delay time determined from signals sensed by mechanical signal sensing circuit 92.

When a predetermined or selected number of pacing delay test settings have been applied, control circuit 80 may determine if a different pacing delay setting needs to be set at block 214. For example, control circuit 80 may execute the process of flow chart 200, in cooperation with therapy delivery circuit 84, cardiac electrical signal sensing circuit 86 and cardiac mechanical sensing circuit 92, for selecting the operating AV delay at block 212 for use in delivering His-Purkinje pacing pulses during an atrial synchronous ventricular pacing mode. However, control circuit 80 may determine that a VV delay remains to be selected at block 214 when ventricular pacing is to be delivered at a second site, e.g., another His-Purkinje pacing site or a myocardial pacing site, to provide multi-site CRT. Control circuit 80 may be configured to apply multiple AV delay settings for selecting an operating AV delay based on sensed cardiac signal analysis. Once the operating AV delay is selected, control circuit 80 may select an operating VV delay by returning to block 204 an repeating the process of blocks 204 through 212 while delivering His-Purkinje pacing pulses to a first pacing site according to the selected AV delay and applying ventricular pacing pulses to a second pacing site according to multiple VV delay test settings from the His-Purkinje pacing pulses. An operating VV delay may be selected at block 212 based on the analysis of features determined from sensed cardiac signals at block 208, which may be the same or different signal features than the signal features determined for selecting an operating AV delay.

In other examples, multiple combinations of AV and VV delays may be applied at block 204 for controlling His-Purkinje pacing pulses delivered at block 206 according to a selected combination of an AV delay and a VV delay. A combination of an AV delay and a VV delay may be selected by control circuit 80 at block 212 based on the analysis of signal features determined at block 208.

The operating pacing delay(s) may be selected at block 212 from among the test pacing delay settings based on a comparative analysis of the signal features determined at block 208. Examples of selection criteria used for selecting an AV delay and/or VV delay are described below in conjunction with FIGS. 5 and 6. Control circuit 80 may control therapy delivery circuit 84 to deliver His-Purkinje pacing pulses at block 216 according to the selected operating pacing delay(s). For example, therapy delivery circuit 84 may generate and deliver a His-Purkinje pacing pulse upon expiration of the selected operating AV delay that is started by control circuit 80 in response to each atrial event, e.g., sensed P-wave or delivered atrial pacing pulse, during an atrial synchronous ventricular pacing mode, which may be denoted as a DDD or VDD pacing mode. Additionally or alternatively, therapy delivery circuit 84 may be configured to generate and deliver a ventricular pacing pulse at a VV delay relative to a delivered His-Purkinje pacing pulse. As indicated above, a His-Purkinje pacing pulse may be delivered to a first pacing site for capturing at least a portion of the His-Purkinje system upon expiration of an AV delay or upon expiration of a ventricular lower rate interval (which may be a temporary rate response interval). A second ventricular pacing pulse may be delivered to a second pacing site at the operating VV delay relative to the His-Purkinje pacing pulse. The second pacing site may be a second His-Purkinje pacing site or a ventricular myocardial pacing site.

Figure 5:
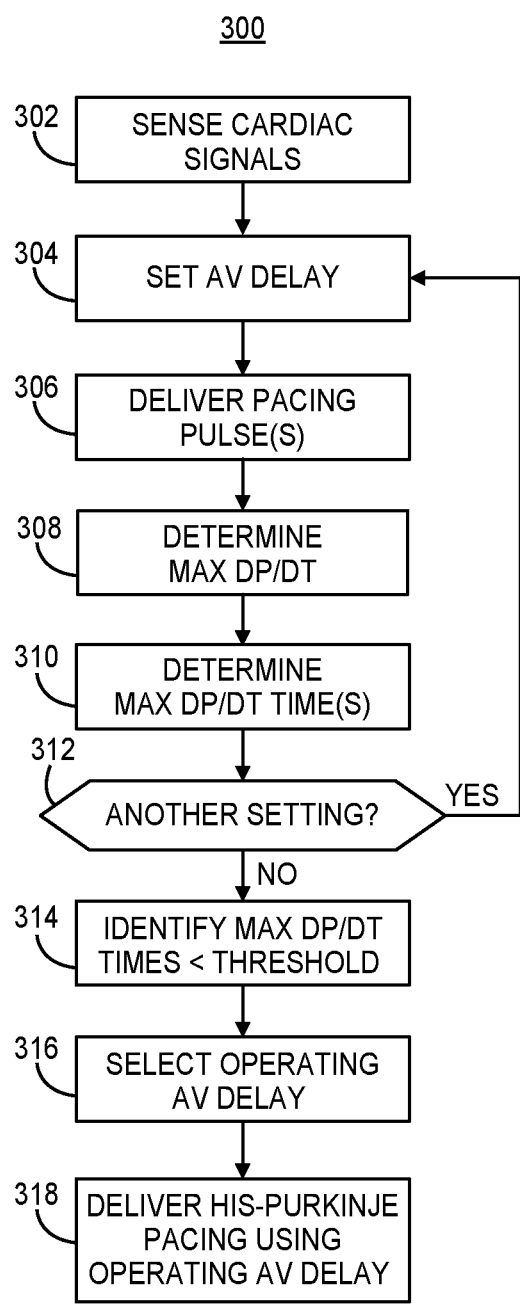
FIG. 5 is a flow chart of a method for setting an operative pacing delay for controlling His-Purkinje pacing pulses according to some examples.

FIG. 5 is a flow chart 300 of a method for setting an operative AV delay according to some examples. At block 302, cardiac electrical signals and ventricular pressure signal(s) are sensed. As described above in conjunction with FIG. 4, control circuit 80 sets an AV delay (block 304) and controls the therapy delivery circuit 84 to deliver His-Purkinje pacing pulses according to the AV delay at block 306. In this example, control circuit 80 determines the maximum dP/dt at block 308 from the ventricular pressure signal(s), which may be an RV pressure signal and/or an LV pressure signal. At block 310, control circuit 80 determines the maximum dP/dt time(s) as the time interval from the delivered His-Purkinje pacing pulse to the maximum dP/dt. In other examples, the maximum dP/dt time(s) may be determined between the maximum dP/dt of a pressure signal and the time of the preceding peak amplitude of a pacing-evoked QRS signal in the near field or far field ventricular EGM signal following the His-Purkinje pacing pulse. A maximum dP/dt time may be determined for each of the RV pressure signal and the LV pressure signal when both pressure signals are being sensed. The maximum dP/dt time is determined by control circuit 80 as an electromechanical time delay between the ventricular electrical event and a fiducial point of the pressure signal.

In some examples, when both an RV pressure signal and an LV pressure signal are being sensed, control circuit 80 may receive both signals and determine an inter-ventricular maximum dP/dt time interval at block 310. The inter-ventricular maximum dP/dt time interval may be determined as the time interval from the maximum peak of the RV dP/dt signal to the maximum peak of the LV dP/dt signal. The inter-ventricular maximum dP/dt time interval may be determined by control circuit 80 as an inter-ventricular mechanical delay time relating to the mechanical synchrony of the ventricular contractions. When multiple AV delay settings are being assessed, control circuit 80 may return to block 304 from block 312 when additional test AV delay settings remain to be applied.

At block 314, control circuit 80 may identify the AV delay settings that are associated with an electromechanical time delay, in this example a maximum dP/dt time, that is less than a threshold time interval. The threshold time interval may be a predetermined value programmed in memory 82 and may be between 40 and 100 ms, between 50 and 80 ms or between 60 and 75 ms as examples. In some examples, control circuit 80 may establish the threshold time interval based on the maximum dP/dt times determined during the process of flow chart 300. For example, the threshold time interval may be set to a percentage of the longest maximum dP/dt time or between the shortest and longest maximum dP/dt times. Each AV delay that results in a maximum dP/dt time that is less than the threshold time interval may be identified as a potential operating AV delay at block 314.

In some examples, instead of applying a threshold time interval, control circuit 80 may identify the AV delay settings associated with a minimum electromechanical time delay, e.g., the shortest maximum dP/dt time determined at block 310. In other examples, the control circuit 80 may require that the AV delays identified at block 314 are associated with maximum dP/dt times that are less than the threshold time interval and greater than a minimum threshold time.

At block 316, control circuit 80 may select the operating AV delay from among the identified AV delays associated with the maximum dP/dt times that are less than the threshold time interval. In some examples, control circuit 80 may select the operating AV delay based on the electromechanical time delay and the maximum dP/dt amplitude. For example, control circuit 80 may select the operating AV delay that resulted in the greatest maximum dP/dt amplitude from among the identified AV delays associated with an electromechanical time delay that is less than a threshold time interval. In still other examples, control circuit 80 may select the operating AV delay as an AV delay setting that resulted in a minimum inter-ventricular mechanical delay time, e.g., a minimum inter-ventricular maximum dP/dt time, from among the AV delays associated with a maximum dP/dt time that is less than the threshold time interval.

After selecting the operating AV delay, control circuit 80 starts the operating AV delay in response to each atrial event, e.g., each atrial pacing pulse and sensed atrial P-wave. Therapy delivery circuit 84 is configured to deliver a His-Purkinje pacing pulse at block 318 at the expiration of each AV delay started by control circuit 80 in response to an atrial sensed event signal received from sensing circuit 86 or an atrial pacing pulse delivered by therapy delivery circuit 84.

While the process of flow chart 300 is described for selecting an operating AV delay, the process of flow chart 300 may be adapted for selecting an operating VV delay by delivering the His-Purkinje pacing pulses at block 306 according to multiple VV delay settings relative to ventricular pacing pulses delivered at a second pacing site during the same ventricular cycle. The maximum dP/dt amplitudes and maximum dP/dt times may be determined at blocks 308 and 310 for each VV delay. An operating VV delay may be selected from among the VV delays identified to be associated with a maximum dP/dt time that is less than a threshold time interval and resulting in a greatest maximum dP/dt amplitude and/or minimum inter-ventricular maximum dP/dt time.

Figure 6:
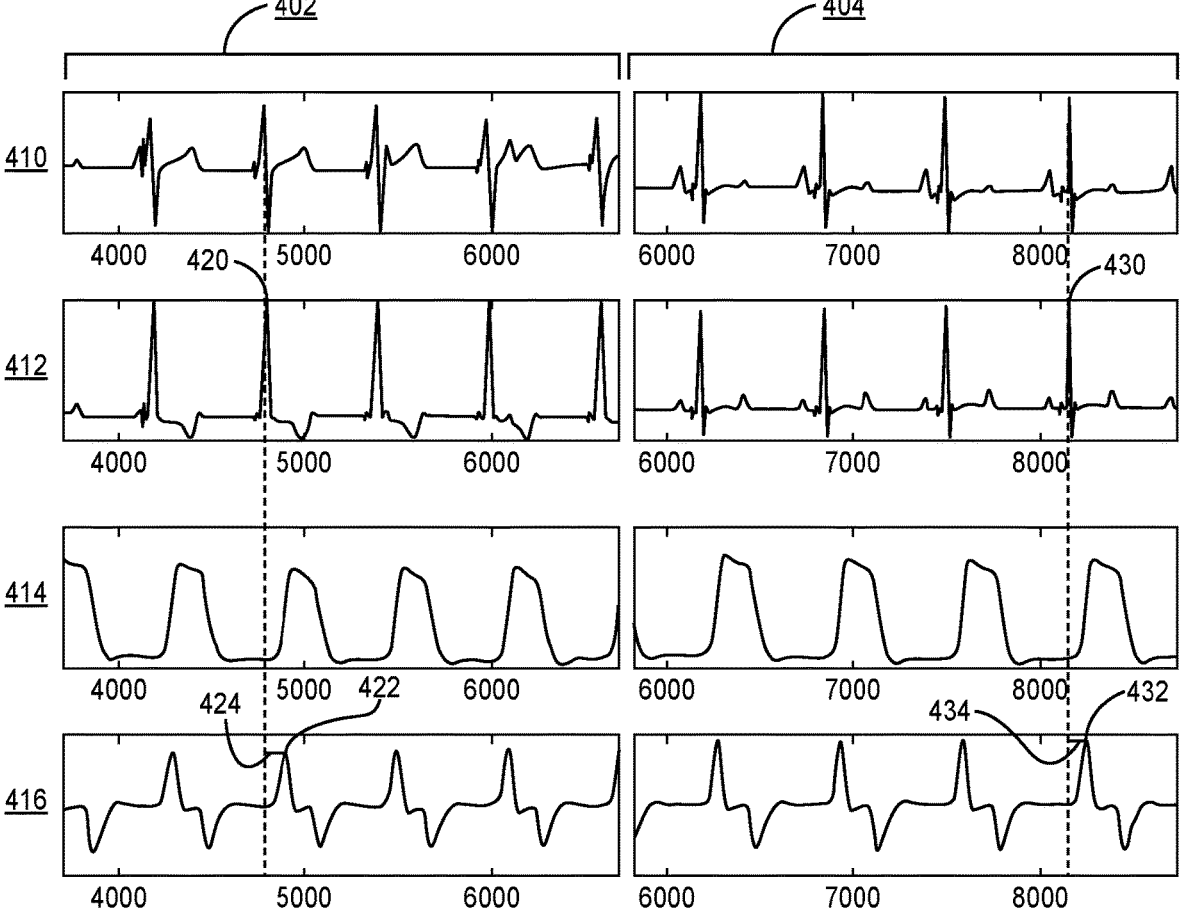
FIG. 6 is a diagram of cardiac signals that may be received by processing circuitry of a medical device for analysis in selecting a pacing delay for controlling His-Purkinje pacing pulses according to some examples.

FIG. 6 is a diagram 400 of cardiac signals that may be received by processing circuitry of a medical device according to some examples. The cardiac signals are sensed during His-Purkinje system pacing in the area of the LBB in this example. The two cardiac electrical signals 410 and 412 are ECG signals (lead II and lead V) in this example. In other examples, a near field and/or far field ventricular EGM signal may be received by the processing circuitry. An LV pressure signal 414 and the LV dP/dt signal 416 which may be determined from the LV pressure signal 414 by the processing circuitry are shown. In other examples, an RV pressure signal may be received by processing circuitry, in addition to or instead of the LV pressure signal. The processing circuitry receiving the ECG signals 410 and 412 and the LV pressure signal 414 may be external device processor 52 in this example. However, it is to be understood that in other examples, the cardiac electrical signals may be EGM signals received by IMD control circuit 80, which may also be configured to receive pressure signal 414 and/or dP/dt signal 416.

The cardiac signals 410, 412, 414 and 416 are sensed during LBB pacing at two different AV delays during time segments 402 and 404. LBB pacing at an AV delay of 140 ms is shown during the first time segment 402. LBB pacing at an AV delay of 100 ms is shown during the second time segment 404. The processing circuitry receiving the sensed cardiac electrical signal signals 410 and 412 may be configured to determine the time of peak 420 of a QRS signal following a His-Purkinje pacing pulse. The processing circuitry receiving the pressure signal 414 may determine a maximum positive dP/dt amplitude 422 following the QRS peak 420 and determine the maximum dP/dt time 424 as the time interval from the QRS peak 420 to the time of the maximum positive dP/dt amplitude 422. The maximum dP/dt time 424 can be determined by the processing circuitry as an electromechanical time delay associated with the AV delay applied during time segment 402.

Similarly, during His-Purkinje pacing at a different AV delay, during time segment 404, the processing circuitry determines the time of a QRS peak 430, determines the maximum positive dP/dt amplitude 432 following the QRS peak 430, and determines the maximum dP/dt time 434 as the time interval from the QRS peak 430 to the time of the maximum positive dP/dt amplitude 432. While the maximum positive dP/dt amplitude and maximum dP/dt time is denoted for a single ventricular cycle during each time interval 402 and 404 in FIG. 6, it is to be understood that the processing circuitry, e.g., external device processor 52 or IMD control circuit 80 receiving the signals shown in FIG. 6, may determine the maximum positive dP/dt amplitude and the maximum dP/dt time for multiple ventricular cycles, following a selected number of His-Purkinje pacing pulses (e.g., 3 to 12 pacing pulses) each delivered at a respective AV delay.

As observed in FIG. 6, the maximum dP/dt time 432 is shorter than the maximum dP/dt time 422. The maximum dP/dt amplitude 432 is greater than the maximum dP/dt amplitude 422. The pacing-evoked QRS signals in ECG signals 410 and 412 are relatively similar during the two different AV delays represented by time segments 402 and 404. The large narrow QRS signals indicate capture of the His-Purkinje system. The improved electrical synchrony achieved by capturing the His-Purkinje system, however, may not result in optimal mechanical synchrony of the heart chambers when His-Purkinje pacing is delivered at different AV delays. As described above, processing circuitry that is configured to receive a cardiac electrical signal and a pressure signal can be configured to determine the maximum dP/dt times 422 and 432 for at least one ventricular cycle during His-Purkinje pacing delivery according to one or more AV delay settings to identify an AV delay setting having a maximum dP/dt time that is less than a threshold time interval.

The threshold time interval may be a predetermined threshold, a threshold set based on a baseline maximum dP/dt time determined from the same patient, which may be determined during no ventricular pacing at all or during pacing at a ventricular myocardial pacing site without His-Purkinje pacing or during His-Purkinje pacing at a nominal AV delay (if the patient has complete AV conduction block and requires some ventricular pacing support). In other examples, the threshold time interval may be set by the processing circuit based on the smallest and/or largest maximum dP/dt times determined from the same patient during His-Purkinje pacing at different AV delay settings.

When an AV delay is identified by the processing circuit as being associated with a maximum dP/dt time that is less than the threshold time interval, the processing circuit may additionally verify that the maximum dP/dt amplitude 432 is greater than a threshold amplitude or is the highest maximum dP/dt amplitude determined from the AV delays associated with maximum dP/dt times that are less than the threshold time interval. Other criteria relating to the cardiac electrical signals 410, 412, pressure signal 414 and/or dP/dt signal 416 may be applied by the processing circuit for selecting an operating AV delay from among the AV delays associated with a maximum dP/dt time that is less than the threshold time interval.

Figure 7:
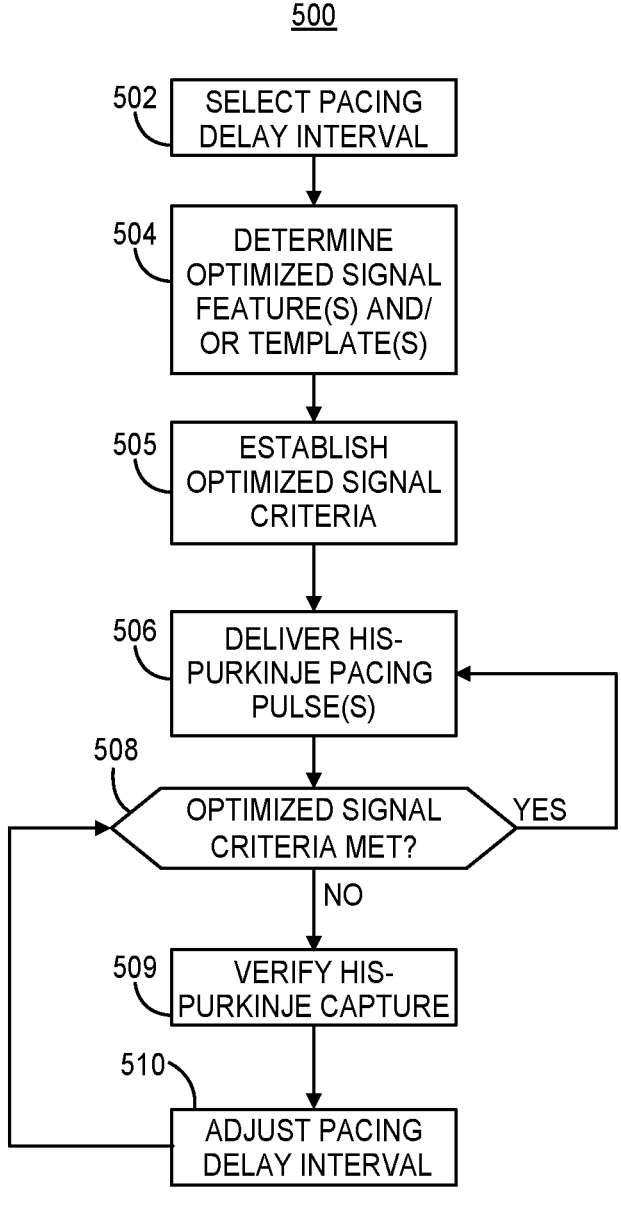
FIG. 7 is a flow chart of a method that may be performed by a medical device for controlling a pacing delay during His-Purkinje pacing according to another example.

FIG. 7 is a flow chart 500 of a method that may be performed by a medical device for controlling a pacing delay interval according to another example. At block 502, control circuit 80 of IMD 14 (or pacemaker 100) may select an operating pacing delay interval, e.g., an AV delay or a VV delay, according to any of the example methods described above. Control circuit 80 may determine one or more signal features or a signal morphology template at block 504 from one or more cardiac signals sensed during His-Purkinje pacing according to the selected operating pacing delay interval. The signal features or signal morphology template may be determined from a near field His-Purkinje EGM signal, a far field ventricular EGM signal, a derivative or difference signal determined from a sensed EGM signal, a pressure signal, an acceleration signal sensed from within the RA or the RV, a derivative or difference signal (e.g., a dP/dt signal) determined from the pressure signal, and/or a derivative or difference signal determined from the acceleration signal, as examples.

In some examples, a signal other than a ventricular pressure signal may be used as a surrogate for the ventricular pressure signal for monitoring for optimized mechanical heart chamber synchrony during His-Purkinje pacing at a selected pacing delay interval. Pressure signal sensing may require relatively high current demands for sensing and signal processing and analysis on a chronic basis such that use of a surrogate sensor signal for monitoring for changes in a cardiac signal that may indicate a need to adjust a His-Purkinje pacing control parameter may conserve power source 98 of IMD 14. In other instances, a pressure signal that is sensed and analyzed for selecting the pacing delay interval may be sensed by a temporary pressure sensor, e.g., placed acutely in the RV or LV, and may not be available for chronic pressure signal sensing and analysis for updating or adjusting the pacing delay interval over time. For example, when the AV delay is selected at block 502 using temporary pressure leads(s) implanted in the RV and/or LV, the temporary pressure lead may be removed after selecting the operating pacing delay interval. During His-Purkinje pacing at the selected operating AV delay (and/or VV delay), a different cardiac signal that is available for chronic sensing and analysis by IMD 14 (or pacemaker 100) may be characterized by determining specific features and/or a waveform morphology template that is representative of the ventricular event signal, e.g., an evoked QRS waveform, pressure waveform, or acceleration waveform, during His-Purkinje pacing according to the selected operating AV delay.

In some examples, as described in conjunction with FIGS. 1A-2B, a lead extending within the RA or the RV may carry an accelerometer or, in the case of pacemaker 100, the accelerometer may be within the pacemaker housing 105. One or more specific signal features and/or a waveform morphology template of the ventricular event signal in the acceleration signal sensed by the accelerometer following one or more His-Purkinje pacing pulses delivered according to the operating AV delay (and/or VV delay) may be determined by control circuit 80. Among the features of a ventricular event signal that may be determined from the acceleration signal by control circuit 80 are a maximum peak amplitude, an area or integration determined by summing acceleration signal sample points, a signal width, a maximum slope, and/or a threshold amplitude crossing time. Other features that may be determined from the acceleration signal are the time interval from the delivered His-Purkinje pacing pulse to the maximum peak of the acceleration signal following the pacing pulse and/or the time interval from the delivered His-Purkinje pacing pulse to the maximum slope of the acceleration signal following the pacing pulse. In other examples, the time interval from the maximum peak of the QRS waveform following the His-Purkinje pacing pulse to the subsequent maximum peak amplitude of the acceleration signal and/or to the maximum slope of the acceleration signal may be determined. These time intervals determined from a ventricular electrical event to a fiducial point of the acceleration signal may be determined as surrogates for the electromechanical time delay determined from a pressure signal for use in selecting an operating pacing delay interval.

In other examples, both an RV and an LV pressure signal may be sensed during a procedure for selecting the operating pacing delay interval at block 502, but only the RV pressure signal may be available for chronic, ambulatory monitoring. In this case, the operating pacing delay interval may be selected based on criteria applied to the LV pressure signal or both the RV and LV pressure signal, e.g., according to any of the example methods described above, but the RV pressure signal and/or RV dP/dt signal may be characterized during His-Purkinje pacing according to the selected operating pacing delay interval for determining specific features and/or the pressure waveform morphology template following His-Purkinje pacing pulses delivered according to the selected operating pacing delay (e.g., AV delay or VV delay or a selected combination of AV delay and VV delay).

The signal features determined at block 504 may be determined as a mean, median, maximum, minimum, range or other representative value(s) of the respective signal feature determined from the cardiac signal sensed over multiple ventricular cycles in some examples. In other examples, a representative value of a signal feature may be determined from an ensemble averaged signal determined by control circuit 80 from the respective cardiac signal that is sensed over multiple ventricular cycles during His-Purkinje pacing according to the operating pacing delay interval. When a waveform morphology template is being determined, the sensed signal, e.g., the pressure, acceleration or EGM signal, may be acquired during a ventricular event window following a His-Purkinje pacing pulse for multiple ventricular cycles, e.g., 3 to 12 cycles, and some or all of the individual signal waveforms acquired during the ventricular event windows may be ensemble averaged to obtain the waveform morphology template and/or for determining specific ventricular event signal features.

Control circuit 80 may be configured to establish optimized signal criteria at block 505 based on the signal features determined at block 504. The optimized signal criteria may define one or more thresholds, ranges or other values or criteria that may be applied by control circuit 80 to one or more of the cardiac electrical signal(s) and/or cardiac mechanical signal(s) sensed during later, subsequent cardiac cycles to verify that a respective signal feature determined at a later time matches, within an acceptable tolerance or normal variation, the analogous feature determined when the operating pacing delay interval was selected at block 502. For example, control circuit 80 may set a threshold or range based on signal feature values determined at block 504 that define an acceptable match to the signal feature that is determined during His-Purkinje pacing at the operating pacing delay interval. To illustrate, a peak amplitude of the acceleration signal may be determined at block 504 and optimized signal criteria may be established to be ±10%, ±15% or ±20% of the acceleration signal peak amplitude. In other examples, the optimized signal criteria may define a threshold as a percentage or portion of the determined signal feature. To illustrate, a maximum acceleration signal slope threshold may be set to 70%, 80% or 90% of the maximum acceleration signal slope determined at block 504.

In still other examples, control circuit 80 may establish a morphology match threshold. When a waveform morphology template is stored for a cardiac signal as a determined signal feature at block 504, control circuit 80 may determine a range of morphology match scores or a minimum morphology match score that occurs between individual cardiac signal waveforms acquired during individual ventricular cycles during His-Purkinje pacing according to the operative pacing delay interval and the established morphology template. A morphology match threshold may be set as a percentage or portion of the minimum of the morphology match scores. The morphology match scores may be determined by performing a wavelet analysis, e.g., using a Haar transform or other techniques, for determining the similarity between the morphology template and a signal waveform acquired during a single ventricular cycle. In other examples, a predetermined morphology match threshold may be stored in memory 82.

The signal features and optimized signal criteria may be determined from more than one cardiac signal at blocks 504 and 505. For example, signal features may be determined from an EGM signal and an RV pressure signal, from an RV pressure signal and an acceleration signal, from an acceleration signal and an EGM signal or from a combination of all three signals. In an illustrative example, a maximum dP/dt time, the maximum peak amplitude of the acceleration signal, and a QRS morphology score may each be determined by control circuit 80 and compared to respective thresholds included in the optimized signal criteria.

At block 506, control circuit 80 controls therapy delivery circuit 84 to deliver His-Purkinje pacing pulses according to the operative AV delay and/or VV delay and any other programmed or established His-Purkinje pacing control parameters. In some examples, the pacing pulse output is adjusted at block 506 as needed to maintain capture of a desired portion of the His-Purkinje system. For example, the pacing electrode vector(s), pacing pulse amplitude and/or pulse width may be selected and adjusted as needed to achieve selective His bundle capture, non-selective His bundle capture, LBB capture, RBB capture, bilateral BB capture (which may be cathodal and anodal capture using a single pacing electrode pair or cathodal capture of both of the RBB and LBB using two different pacing electrode pairs). Capture of the His-Purkinje system may be determined based on an analysis of the sensed cardiac electrical signals, e.g., using the techniques generally disclosed in the above-incorporated U.S. patent application Ser. No. 17/533,005 (Cao, et al.).

At block 508, control circuit 80 may analyze sensed cardiac signals to determine if the optimized signal criteria are met. Control circuit 80 may perform the analysis at block 508 on a beat-by-beat or less frequent basis. In some examples, control circuit 80 may be configured to perform a His-Purkinje capture threshold test once a day, for example during the night while the patient is asleep, or according to another capture threshold testing schedule. The analysis at block 508 may be performed in conjunction with a capture threshold test, e.g., after verifying a desired type of His-Purkinje system capture and setting the associated pacing pulse output electrode vector, pulse amplitude and pulse width for promoting His-Purkinje capture.

During His-Purkinje pacing at the current value of the operating pacing delay interval, control circuit 80 may determine one or more signal features from one or more sensed cardiac signals. Signal features determined at block 504, which may include obtaining a signal waveform over a ventricular event window, may be determined at block 508 from the acceleration signal, pressure signal(s), and/or EGM signal(s) that are sensed by IMD 14 (or pacemaker 100). The determined signal features may be compared to the optimized signal criteria at block 508 to determine if the mechanical synchrony achieved when the operating pacing delay was selected is still being achieved. If the optimized signal criteria are not met at block 508, control circuit 80 may adjust the pacing delay interval at block 510.

In some instances, the optimized signal criteria may be unmet when loss of capture of the His-Purkinje system occurs. Accordingly, in some examples, control circuit 80 may verify capture of the His-Purkinje system at block 509, e.g., by analyzing the cardiac electrical signals received from sensing circuit 86. Techniques disclosed in the above-incorporated references may be used for determining capture of the His-Purkinje system. In some cases, the pacing pulse output may be adjusted at block 509 to promote capture of at least a portion of the His-Purkinje system according to a desired capture type, e.g., to provide capture of the His bundle and/or one or both of the LBB and the RBB. After verifying capture, control circuit 80 may determine if optimized signal criteria are still unmet and proceed to block 510. It is to be understood that, if control circuit 80 adjusts the pacing pulse output, e.g., pacing pulse amplitude and/or pacing pulse width, and/or a pacing electrode vector selection for delivering His-Purkinje pacing pulses to re-establish capture of a targeted portion of the His-Purkinje system (and/or ventricular myocardium during CRT), further adjustment of a pacing delay interval may not be required at block 510. Re-establishing His-Purkinje capture may result in the optimized signal criteria being met.

In other instances, after optionally verifying capture at each targeted capture site, the optimized signal criteria may remain unmet. An adjustment to a pacing delay interval may be made to restore the optimized signal feature(s). In some examples, control circuit 80 may adjust a pacing delay interval at block 510 by increasing or decreasing the AV or VV delay by a predetermined amount, e.g., by 10 to 20 ms. Therapy delivery circuit 84 may deliver the His-Purkinje pacing pulses at the adjusted pacing delay interval at block 506. The signal features may be re-determined by control circuit 80 from the cardiac signal(s) sensed during His-Purkinje pacing according to the adjusted pacing delay interval at block 508 and compared to the optimized signal criteria by control circuit 80. This process of redetermining signal features and comparing the signal features to optimized signal criteria may be repeated for multiple pacing delay settings until the sensed cardiac signal feature(s) meet the optimized signal criteria at block 508. Once the optimized signal criteria are met at an adjusted pacing delay interval, the adjusted pacing delay interval may be set as the operating pacing delay interval by control circuit 80. Control circuit 80 may return to block 506 to control therapy delivery circuit 84 to deliver His Purkinje pacing pulses according to the new operating pacing delay interval until the next time optimized signal criteria are determined to be unmet at block 508.

In other examples, when the optimized signal criteria are not met at block 508, control circuit 80 may return to block 502 from block 508 (path not illustrated in FIG. 7) to select a new operating pacing delay based on an analysis of the pressure signal according to the techniques described above. Sensed cardiac signals may be subsequently monitored by control circuit 80 for detecting when optimized signal criteria are no longer met at block 508. When optimized signal criteria are not met, control circuit 80 may return to block 502 to sense at least one pressure signal for analysis for selecting an operating pacing delay interval according to any of the example techniques described above.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device, comprising:

a therapy delivery circuit configured to deliver at least one His-Purkinje pacing pulse according to each of a plurality of settings of a pacing control parameter;

a pressure sensor configured to sense a first pressure signal; and a processing circuit configured to:

for each of the plurality of settings of the pacing control parameter:

identify a ventricular electrical event;

identify a fiducial point of the first pressure signal following the ventricular electrical event;

determine an electromechanical time delay from the ventricular electrical event to the fiducial point of the first pressure signal;

identify from among the plurality of settings of the pacing control parameter each pacing control parameter setting that is associated with a determined electromechanical time delay that is less than a threshold interval; and for each of the identified pacing control parameter settings associated with a determined electromechanical time delay that is less than the threshold interval, determine a maximum slope amplitude of the pressure signal;

select an operating pacing control parameter from the identified pacing control parameter settings as one of the identified pacing control parameter settings that is associated with a greatest maximum slope amplitude of the determined maximum slope amplitudes;

wherein the therapy delivery circuit is configured to deliver His-Purkinje pacing pulses according to the selected operating pacing control parameter.

2. The medical device of claim 1, wherein the processing circuit is further configured to identify the fiducial point of the first pressure signal by determining the maximum slope of the first pressure signal.

3. The medical device of claim 1, further comprising a sensing circuit configured to sense a cardiac electrical signal;

wherein the processing circuit is further configured to identify the ventricular electrical event as one of:

a pacing pulse delivered by the therapy delivery circuit; or a reference point of a QRS waveform of the cardiac electrical signal.

4. The medical device of claim 1, wherein:

the pressure sensor is further configured to sense a second pressure signal; and the processing circuitry is further configured to:

for each of the plurality of settings of the pacing control parameter, determine a mechanical delay time from a first point of the first pressure signal to a second point of the second pressure signal;

determine a minimum mechanical delay time from the determined mechanical delay times; and select the operating pacing control parameter as one of the identified pacing control parameter settings that is associated with the minimum mechanical delay time.

5. The medical device of claim 1, wherein the processing circuitry is further configured to identify each of the pacing control parameter settings from among the plurality of settings of the pacing control parameter that is associated with a determined electromechanical time delay that is less than the threshold interval and greater than a minimum threshold interval.

6. The medical device of claim 1, further comprising a second sensor for sensing a second signal;

wherein the processing circuit is further configured to:

determine a feature of the second signal sensed following a His-Purkinje pacing pulse delivered according to the operating pacing control parameter;

determine that optimized signal criteria are not met by the feature of the second signal; and adjust the operating pacing control parameter in response to the optimized signal criteria not being met.

7. The medical device of claim 6, wherein the second sensor comprises one of a second pressure sensor configured to sense a second pressure signal or an accelerometer configured to sense an acceleration signal.

8. The medical device of claim 6, wherein the processing circuit is further configured to, in response to selecting the operating pacing control parameter, establish the optimized signal criteria based on an analysis of the second signal sensed by the second sensor following at least one His-Purkinje pacing pulse delivered by the therapy delivery circuit according to the selected operating pacing control parameter.

9. The medical device of claim 1, wherein:

the therapy delivery circuit is configured to deliver at least one His-Purkinje pacing pulse at each of the plurality of settings of the pacing control parameter by delivering at least one His-Purkinje pacing pulse at an expiration of each of a plurality of atrioventricular delay settings; and the processing circuit is configured to select the operating pacing control parameter from the identified pacing control parameter settings by selecting an operating atrioventricular delay.

10. The medical device of claim 9, wherein:

the therapy delivery circuit is further configured to:

generate the His-Purkinje pacing pulses for delivery to a first pacing site;

generate second ventricular pacing pulses for delivery to a second pacing site different than the first pacing site; and deliver His-Purkinje pacing pulses according to each of a plurality of inter-ventricular delay settings relative to the second ventricular pacing pulses; and the processing circuit is further configured to:

for each of the plurality of inter-ventricular delay settings, determine a feature of the first pressure signal; and select an operating inter-ventricular delay based on the determined features of the first pressure signal; and the therapy delivery circuit is configured to:

deliver the His-Purkinje pacing pulses according to the operating pacing control parameter by delivering each His-Purkinje pacing pulse at an expiration of the selected operating atrioventricular delay; and deliver the second ventricular pacing pulses at the operating inter-ventricular delay relative to each of the His-Purkinje pacing pulses.

11. The medical device of claim 1, wherein:

the therapy delivery circuit is further configured to:

generate the His-Purkinje pacing pulses for delivery to a first pacing site;

generate second ventricular pacing pulses for delivery to a second pacing site different than the first pacing site; and deliver at least one His-Purkinje pacing pulse according to each of the plurality of settings of the pacing control parameter by delivering at least one His-Purkinje pacing pulse at each of a plurality of inter-ventricular delay settings relative to the second ventricular pacing pulses; and the processing circuit is further configured to select the operating pacing control parameter from the identified pacing control parameter settings by selecting an operating inter-ventricular delay.

12. A method, comprising:

delivering at least one His-Purkinje pacing pulse according to each of a plurality of settings of a pacing control parameter;

sensing a first pressure signal;

for each of the plurality of settings of the pacing control parameter:

identifying a ventricular electrical event;

identifying a fiducial point of the first pressure signal following the ventricular electrical event; and determining an electromechanical time delay from the ventricular electrical event to the fiducial point of the first pressure signal;

identifying from among the plurality of settings of the pacing control parameter each of the pacing control parameter settings that is associated with a determined electromechanical time delay that is less than a threshold interval;

for each of the identified pacing control parameter settings associated with a determined electromechanical time delay that is less than the threshold interval, determining a maximum slope amplitude of the pressure signal;

selecting an operating pacing control parameter from the identified pacing control parameter settings that is associated with a greatest maximum slope amplitude of the determined maximum slope amplitudes; and delivering His-Purkinje pacing pulses according to the selected operating pacing control parameter.

13. The method of claim 12, further comprising:

sensing a cardiac electrical signal; and identifying the ventricular electrical event as one of:

a pacing pulse delivered by the therapy delivery circuit; or a fiducial point of a QRS waveform of the cardiac electrical signal.

14. The method of claim 12, further comprising:

sensing a second pressure signal; and for each of the plurality of settings of the pacing control parameter, determining a mechanical delay time from a first point of the first pressure signal to a second point of the second pressure signal;

determining a minimum mechanical delay time from the determined mechanical delay times; and selecting the operating pacing control parameter as one of the identified pacing control parameter settings that is associated with the minimum mechanical delay time.

15. The method of claim 12, further comprising:

sensing a second signal, wherein sensing the second signal comprises sensing one of a second pressure signal or an acceleration signal;

determining a feature of the second signal sensed following a His-Purkinje pacing pulse delivered according to the operating pacing control parameter;

determining that optimized signal criteria are not met by the feature of the second signal; and adjusting the operating pacing control parameter in response to the optimized signal criteria not being met.

16. The method of claim 15, further comprising, in response to selecting the operating pacing control parameter, establishing the optimized signal criteria based on an analysis of the second signal following at least one His-Purkinje pacing pulse delivered according to the selected operating pacing control parameter.

17. The method of claim 12, further comprising:

delivering at least one His-Purkinje pacing pulse at each of the plurality of settings of the pacing control parameter by delivering at least one His-Purkinje pacing pulse at an expiration of each of a plurality of atrioventricular delay settings; and selecting the operating pacing control parameter from the identified pacing control parameter settings by selecting an operating atrioventricular delay.

18. The method of claim 12, further comprising:

generating the His-Purkinje pacing pulses for delivery to a first pacing site;

generating second ventricular pacing pulses for delivery to a second pacing site different than the first pacing site;

delivering at least one His-Purkinje pacing pulse according to each of the plurality of settings of the pacing control parameter by delivering at least one His-Purkinje pacing pulse at each of a plurality of inter-ventricular delay settings relative to the second ventricular pacing pulses; and selecting the operating pacing control parameter from the identified pacing control parameter settings by selecting an operating inter-ventricular delay.

19. A non-transitory, computer-readable storage medium comprising a set of instructions which, when executed by a processing circuit of a medical device cause the medical device to:

deliver at least one His-Purkinje pacing pulse according to each of a plurality of settings of a pacing control parameter;

sense a pressure signal;

for each of the plurality of settings of the pacing control parameter:

identify a ventricular electrical event;

identify a fiducial point of the pressure signal following the ventricular electrical event; and determine an electromechanical time delay from the ventricular electrical event to the fiducial point of the pressure signal;

identify from among the plurality of settings of the pacing control parameter each of the pacing control parameter settings that is associated with a determined electromechanical time delay that is less than a threshold interval;

for each of the identified pacing control parameter settings associated with a determined electromechanical time delay that is less than the threshold interval, determine a maximum slope amplitude of the pressure signal;

select an operating pacing control parameter from the identified pacing control parameter settings that is associated with a greatest maximum slope amplitude of the determined maximum slope amplitudes; and deliver His-Purkinje pacing pulses according to the selected operating pacing control parameter.

* * * * *